United States Patent
Raboisson et al.

(10) Patent No.: US 9,290,502 B2
(45) Date of Patent: Mar. 22, 2016

(54) PTERIDINES USEFUL AS HCV INHIBITORS AND METHODS FOR THE PREPARATION THEREOF

(71) Applicant: Tibotec Pharmaceuticals Ltd., Little Island, Co Cork (IE)

(72) Inventors: Pierre Jean-Marie Bernard Raboisson, Sterrebeek (BE); Dominique Louis Nestor Ghislain Surleraux, Braine-le-chateau (BE); Tse-I Lin, Mechelen (BE); Oliver Lenz, Sint-Katelijne-Waver (BE); Kenneth Alan Simmen, Tervuren (BE)

(73) Assignee: JANSSEN SCIENCES IRELAND UC, Little Island, County Cork (IE)

( * ) Notice: Subject to any disclaimer, the term of this patent is extended or adjusted under 35 U.S.C. 154(b) by 38 days.

(21) Appl. No.: 14/095,099

(22) Filed: Dec. 3, 2013

(65) Prior Publication Data
US 2014/0094468 A1 Apr. 3, 2014

Related U.S. Application Data

(62) Division of application No. 11/914,018, filed as application No. PCT/EP2006/062289 on May 12, 2006, now abandoned.

(60) Provisional application No. 60/680,393, filed on May 12, 2005.

(30) Foreign Application Priority Data

Jul. 7, 2005 (EP) ..................................... 05106212
Apr. 6, 2006 (EP) ..................................... 06075854

(51) Int. Cl.
*A61K 31/495* (2006.01)
*C07D 487/04* (2006.01)
(Continued)

(52) U.S. Cl.
CPC ............ *C07D 487/04* (2013.01); *A61K 31/519* (2013.01); *C07D 475/10* (2013.01)

(58) Field of Classification Search
CPC ........................ A61K 31/4985; A61K 31/519
USPC ......................................................... 514/249
See application file for complete search history.

(56) References Cited

U.S. PATENT DOCUMENTS

| 3,873,545 A | 3/1975 | Osselaere et al. |
| 5,852,028 A | 12/1998 | Suto et al. |

(Continued)

FOREIGN PATENT DOCUMENTS

| GB | 2295387 | 5/1996 |
| JP | 2003/0321472 | 11/2003 |

(Continued)

OTHER PUBLICATIONS

Bataller et al. "Hepatitis C virus core and Nonstructural protein induce fibrogenic effects in hepatic stellate cells," Gastroenterology, 2004, vol. 126, pp. 529-540.*

(Continued)

*Primary Examiner* — Shengjun Wang
(74) *Attorney, Agent, or Firm* — Baker & Hostetler LLP

(57) ABSTRACT

The present invention relates to the use of pteridines as inhibitors of HCV replication as well as their use in pharmaceutical compositions aimed to treat or combat HCV infections. In addition, the present invention relates to compounds per se and their use as medicines. The present invention also concerns processes for the preparation of such compounds, pharmaceutical compositions comprising them, and combinations of said compounds with other anti-HCV agents.

12 Claims, 1 Drawing Sheet

(51) Int. Cl.
A61K 31/519 (2006.01)
C07D 475/10 (2006.01)

(56) References Cited

U.S. PATENT DOCUMENTS

| | | | |
|---|---|---|---|
| 5,935,966 | A | 8/1999 | Suto et al. |
| 6,184,226 | B1 | 2/2001 | Chakravarty et al. |
| 6,277,989 | B1 | 8/2001 | Chakravarty et al. |
| 6,476,031 | B1 | 11/2002 | Chakravarty et al. |
| 8,030,318 | B2 | 10/2011 | Simmen et al. |
| 2004/0032430 | A1 | 2/2004 | Yung et al. |
| 2004/0038856 | A1 | 2/2004 | Chakravarty et al. |
| 2004/0132159 | A1 | 7/2004 | Zhong et al. |
| 2005/0004143 | A1 | 1/2005 | Dugar et al. |
| 2007/0155716 | A1 | 7/2007 | Simmen et al. |
| 2008/0182863 | A1 | 7/2008 | Simmen et al. |
| 2009/0131460 | A1 | 5/2009 | Simmen et al. |
| 2009/0156595 | A1 | 6/2009 | Roboisson et al. |

FOREIGN PATENT DOCUMENTS

| | | |
|---|---|---|
| WO | WO 95/19774 | 7/1995 |
| WO | WO 98/38171 | 9/1998 |
| WO | WO 00/12497 | 3/2000 |
| WO | WO 01/47921 | 7/2001 |
| WO | WO 02/22601 | 3/2002 |
| WO | WO 02/076976 | 10/2002 |
| WO | WO 03/059913 | 7/2003 |
| WO | WO 03/077921 | 9/2003 |
| WO | WO 03/078423 | 9/2003 |
| WO | WO 03/078426 | 9/2003 |
| WO | WO 03/078427 | 9/2003 |
| WO | WO 03/097615 | 11/2003 |
| WO | WO 2004/020584 | 3/2004 |
| WO | WO 2004/024159 | 3/2004 |
| WO | WO 2004/047818 | 6/2004 |
| WO | WO 2004/048930 | 6/2004 |
| WO | WO 2004/065392 | 8/2004 |
| WO | WO 2004/074270 | 9/2004 |
| WO | WO 2004/087056 | 10/2004 |
| WO | WO 2005/032481 | 4/2005 |
| WO | WO 2006/100310 | 9/2006 |
| WO | WO 2006/105063 | 10/2006 |

OTHER PUBLICATIONS

Breipohl et al., "Novel Synthetic Routes to PNA Monomers and PNA-DNA Linker Molecules", Tetrahedron, 1997, 53(43), 14671-14686.
Cheng et al., "Hepatitis C Viral Proteins Interact with Smad3 and Differentially Regulate Tgf-β/Smad3-Mediated Transcriptional Activation", Oncogene, Oct. 14, 2004, 23(47), 7821-7838.
Choo et al., "Isolation of a eDNA Clone Derived from a Blood-Borne Non-A, Non-B Viral Hepatitis Genome", Science, 1989, 244, 359-362.
Cooper et al., "Bicyclo[3.3.O]octenones in Synthesis. An Approach to the Synthesis of the Antitumor Sesquiterpene Quadrone", Journal of the Chemical Society, Perkin Transactions, 1984, 1, 799-809.
Crawford et al., "Thrombospondin-1 is a Major Activator of TGF-β1 in Vivo", Cell, Jun. 26, 1998, 93(7), 1159-1170.
Cywin et al., "Discovery and SAR of Novel [1,6]N Aphthyridines as Potent Inhibitors of Spleen Tyrosine Kinase (SYK)", Bioorganic & Medicinal Chemistry Letters, Apr. 17, 2003, 13(8), 1415-1418.
De Caestecker et al., "Role of Transforming Growth Factor-β Signaling in Cancer", Journal of the National Cancer Institute, Sep. 6, 2000, 92(17), 1388-1402.
De Mitri et al., "HCV-Associated Liver Cancer Without Cirrhosis", The Lancet, 1995, 345(8947), 413-415.
Derynck et al., "TGF-β Receptor Signaling", Biochimica et Biophysica Acta, Oct. 24, 1997, 1333(2), F105-F150.
Dorwald, "Side Reactions in Organic Synthesis", Wiley-VCH, Weinheim, p. IX of Preface, 2005, 390 pages.

Dowd et al., "Free Radical Ring-Expansion Leading to Novel Six- and Seven-Membered Heterocycles", Tetrahedron, 1991, 47(27), 4847-4860.
Dumont et al., "Transforming Growth Factor-β and Breast Cancer Tumor Promoting Effects of Transforming Growth Factor-β", Breast Cancer Research, Feb. 21, 2000, 2(2),125-132.
Ettmayer et al., "Lessons Learned from Marketed and Investigational Prodrugs", Journal of Medicinal Chemistry, May 6, 2004, 47(10), 2394-2404.
Gibson et al, "A Novel Method for Real Time Quantitative RT-PCR", Genome Research, 1996, 6, 995-1001.
Goodman and Gilman, "The Pharmacological Basis of Therapeutics: Biotransformation of Drugs", Pergamon Press, 8th Ed., 1990, 13-15.
Greco et al., "Highly Stereoselective Synthesis of Substituted Hydrindanes Related to the Antielepileptic Drug Topiramate", Tetrahedeon Letters, Aug. 25, 1992, 33(35), 5009-5012.
Harrison et al., "The Synthesis of Some Cyclic Hydroxamic Acids from O-Aminocarboxylic Acids", Journal of the Chemical Society Abstracts, 1960, 2157-2160.
Kim, "The Burden of Hepatitis C in the United States", Hepatology, 2002, 36(5), S30-S34.
Kimura et al., "Association of Transforming Growth Factor-β1 Functional Polymorphisms with Natural Clearance of Hepatitis C Virus", The Journal of Infectious Diseases, Brief Report, 2006, 193, 1371-1374.
Kolykhalov et al., "Hepatitis C Virus-Encoded Enzymatic Activities and Conversed RNA Elements in the 3, Nontranslated Region Are Essential for Virus Replication In Vivo", Journal of Virology, 2000, 74(4), 2046-2051.
Krieger et al., "Enhancement of Hepatitis C Virus RNA Replication by Cell Culture-Adaptive Mutations", Journal of Virology, 2001, 75(10), 4614-4624.
Lauer et al., "Hepatitis C Virus Infection", N Engl J Med, 2001, 345(1), 41-52.
Lawrence, "Transforming Growth Factor-β: a general review", Euro. Cytokine Network, Sep. 1996, 7(3), 363-374.
Lin et al., "Expression Cloning of the TGF-β Type II Receptor, a Functional Transmembrane Serine/Threonine Kinase", Cell, Feb. 21, 1992, 68, 775-785.
Lohmann, et al., "Replication of Subgenomic Hepatitis C Virus RNAs in a Hepatoma Cell Line", Science, 1999, 285, 110-113.
Lopez-Casillas et al., "Betaglycan Presents Ligand to the TGFβ Signaling Receptor", Cell, Jul. 2, 1993, 73, 1435-1444.
Lopez-Casillas, "Structure and Expression of the Membrane Proteoglycan Betaglycan, a Component of the TGF-β Receptor System", Cell, Nov. 15, 1991, 67, 785-795.
Lyons et al., "Transforming Growth Factors and the Regulation of Cell Proliferation", European Journal of Biochemistry, Feb. 14, 1990, 187, 467-473.
Massague, "Receptors for the TGF-β Family", Cell, Jun. 26, 1992, 69, 1067-1070.
Massague, "TGF-β Signal Transduction", Annual Review Biochemistry, 1998, 67, 753-791.
Massague, J., "The Transforming Growth Factor-β Family", Annual Review Biochemistry, 1990, 6, 597-641.
Miyazono et al., "TGF-β Signaling by Smad Proteins", Advances in Immunology, 2000, 75, 115-157.
Moyer et al., "Intramolecular N—H, O—H and S—H Insertion Reactions. Synthesis of Heterocycles from α-Diazo β-Keto Esters", Journal of Organic Chemistry, 1985, 50, 5223-5230.
Munger et al., "Latent Transforming Growth Factor-β: Structural Features and Mechanisms of Activation", Kidney International, 1997, 51, 1376-1382.
Munger et al., "The Integrin αvβ6 Binds and Activates Latent TGFβ1: A Mechanism for Regulating Pulmonary Inflammation and Fibrosis", Cell, Feb. 5, 1999, 96, 319-328.
Murata et al., "Suppression of Hepatitis C Virus Replicon by TGF-β", Virology, 2005, 331, 407-417.
"National Institutes of Health Consensus Development Conference Statement: Management of Hepatitis C: Jun. 10-12, 2002", Hepatology, Nov. 2002, S3-S20.

(56) References Cited

OTHER PUBLICATIONS

Nishikawa et al., "Cytokinin Activity of 4-Aminopyridopyrimidines Towards the Growth of Tobacco Callus", Bioscience Biotechnology Biochemistry, 1994, 58(9), 1709-1710.

Nogradi, "Dimethyi-13-Cyclodextrin", Drugs of the Future, 1984, 9(8), 577-578.

Roberts et al., "Transforming Growth Factor-βs", Handbook of Experimental Pharmacology, 1990, 95, 419-459.

Sekiguchi et al., "Reduction of Virus Burden-Induced Splenectomy in Patients with Liver Cirrhosis Related to Hepatitis C Virus Infection", World Journal of Gastroenterology, Apr. 17, 2006, 12(13), 2089-2094.

Stella, "Prodrugs as Therapeutics", Expert Opinion on Therapeutic Patents, 2004, 14(3), 277-280.

Testa, "Prodrug Research: Futile or Fertile?", Biochemical Pharmacology, 2004, 68, 2097-2106.

Van Schayck et al. "Detecting Patients at a High Risk of Developing Chronic Obstructive Pulmonary Disease in General Practice: Cross Sectional Case Finding Study", BMJ, Jun. 8, 2002, 324, 1-5.

Verecek et al., "Neighboring Group Interaction in Ortho-Substituted Heterocycles.2. 1,2,4-Oxadiazolylpyridines and Pyrido[2,3-d]pyrimidine 3-0xides", Journal of Organic Chemistry, 1979, 44(10), 1695-1699.

Wahl et al., "Inflammatory and Immunomodulatory Roles of TGF-β", Immunology Today, 1989, 10(8), 258-261.

Wamhoff, et al., "Dihalogentriphenylphosphorane in der Heterocyclensynthese, 29. Eine einfache Synthese von Pteridin-4-onen aus 3-Amino-2-pyrazincarbonsauremethylester und Pyrazino[3,1]oxazin-4-onen", Synthesis, 1994, 405-410.

Wang et al., "Expression Cloning and Characterization of the TGF-β Type III Receptor", Cell, Nov. 15, 1991, 67, 797-805.

Whitman, "Smads and Early Developmental Signaling by the TGFβ Superfamily", Genes & Development, 1998, 12, 2445-2462.

Wolff (Ed.), "Burger's Medicinal Chemistry and Drug Discovery", vol. 1: Principles and Practice, 5th Edition, John Wiley and Sons, Inc., New York, 1995, Chapter 23, 975-977.

Wolff et al., "Thia Steriods. III. Derivatives of 2-Thia-A-nor-5α-androstan-17β-ol As Probes of Steriod-Receptor Interactions", Journal of Medicinal Chemistry, 1970, 13(3), 531-534.

Wrana et al., "TGFβ Signals Through a Heteromeric Protein Kinase Receptor Complex", Cell, Dec. 11, 1992, 71, 1003-1014.

\* cited by examiner

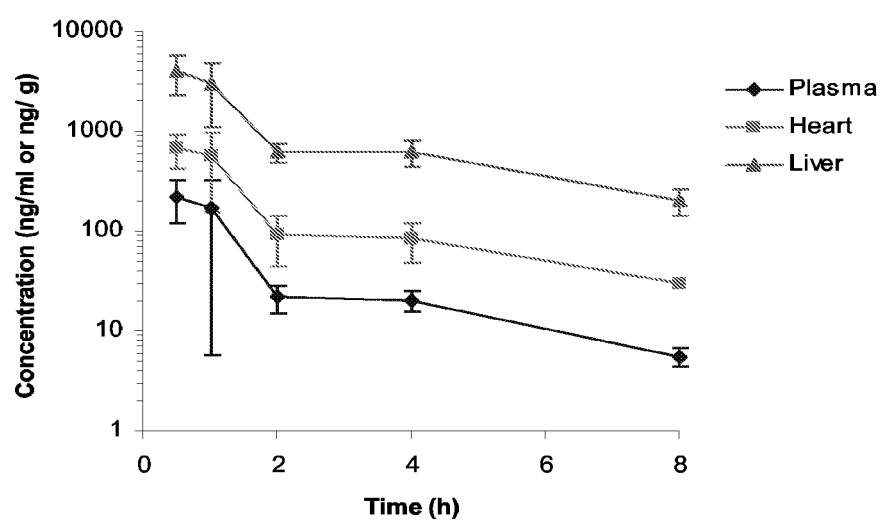

PTERIDINES USEFUL AS HCV INHIBITORS AND METHODS FOR THE PREPARATION THEREOF

CROSS REFERENCE TO RELATED APPLICATIONS

This application is a divisional of U.S. application Ser. No. 11/914,018, filed Jun. 20, 2008, which is the National Stage entry of International Application No. PCT/EP2006/062289, filed May 12, 2006, which claims the benefit of U.S. Provisional Application No. 60/680,393, filed May 12, 2005, EP 05106212.3, filed Jul. 7, 2005, and EP 06075854.7, filed Apr. 6, 2006, the entireties of which are incorporated by reference herein.

The present invention relates to the use of pteridines as inhibitors of HCV replication as well as their use in pharmaceutical compositions aimed to treat or combat HCV infections. In addition, the present invention relates to compounds per se and their use as medicines. The present invention also concerns processes for the preparation of such compounds, pharmaceutical compositions comprising them, and combinations of said compounds with other anti-HCV agents.

Following its discovery in 1989 as the agent implicated in the majority of viral non-A, non-B hepatitis (Choo et al., *Science* 244, 359-362, 1989), hepatitis C virus (HCV) has become a focus of considerable medical research (Lauer, G. M and Walker, B. D., *New Eng. J. Med.* 345, 41-52, 2001). HCV is a member of the Flaviviridae family of viruses in the *hepacivirus* genus, and is closely related to the *flavivirus* genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA in chimpanzee models of infection (Kolykhalov, A. A., Mihalik, K., Feinstone, S. M., and Rice, C. M. *J. Virol.* 74, 2046-2051, 2000). In addition to the NS3 serine protease, HCV also encodes a metalloproteinase in the NS2 region.

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus (HCV). Following the initial acute infection, a majority of infected individuals develop chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. *Hepatology,* 36, 5 Suppl. S3-S20, 2002). Liver cirrhosis due to HCV infection is responsible for about 10,000 deaths per year in the U.S.A. alone, and is the leading cause for liver transplantations. Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades (Kim, W. R. *Hepatology,* 36, 5 Suppl. S30-S34, 2002).

The treatment of this chronic disease is an unmet clinical need, since current therapy is only partially effective and limited by undesirable side effects.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, combination therapy has significant side effects and is poorly tolerated in many patients. For instance, in registration trials of pegylated interferon and ribavirin, significant side effects resulted in discontinuation of treatment in approximately 10 to 14 percent of patients. Major side effects of combination therapy include influenza-like symptoms, hematologic abnormalities, and neuropsychiatric symptoms. The development of more effective, convenient and tolerated treatments is a major public health objective.

Thus, there is a high medical need for low molecular weight compounds that lead to an inhibition of HCV replication.

It has been surprisingly found that derivatives of pteridines exhibit antiviral activity in mammals infected with HCV, in particular these derivatives inhibit HCV replication. These compounds are therefore useful in treating or combating HCV infections.

US20040038856 discloses methods of treating fibroproliferative disorders associated with TGF-β signaling, by administering non-peptide small molecule inhibitors of TGF-β specifically binding to the type I TGF-β receptor (TGFβ-R1). The inhibitors are preferably quinazoline derivatives.

WO04/048930 further describes methods for counteracting a loss in β-adrenergic sensitivity in the β-adrenergic signal transduction pathway by administering an effective amount of a compound capable of inhibiting TGF-β signaling through a TGF-β receptor.

WO04/065392 relates to condensed pyridines and pyrimidines and their use as ALK-5 receptor ligands. In particular, the invention discloses therapeutically active substituted quinoline and quinazoline compounds, the use thereof in therapy, particularly in the treatment or prophylaxis of disorders characterised by overexpression of transforming growth factor β (TGF-β), and pharmaceutical compositions for use in such therapy.

After initial exposure to the Hepatitis C virus, HCV RNA can be detected in blood in 1-3 weeks. Within an average of 50 days virtually all patients develop liver cell injury. The majority of patients are asymptomatic and anicteric. Only 25-35 percent develop malaise, weakness, or anorexia, and some become icteric. Antibodies to HCV (anti-HCV) almost invariably become detectable during the course of illness. Anti-HCV can be detected in 50-70 percent of patients at the onset of symptoms and in approximately 90 percent of patients 3 months after onset of infection. HCV infection is self-limited in only 15 percent of cases. Recovery is characterized by disappearance of HCV RNA from blood and return of liver enzymes to normal.

About 85 percent of HCV-infected individuals fail to clear the virus by 6 months and develop chronic hepatitis with persistent, although sometimes intermittent, viremia. This capacity to produce chronic hepatitis is one of the most striking features of HCV infection. Chronic hepatitis C is typically an insidious process, progressing, if at all, at a slow rate without symptoms or physical signs in the majority of patients during the first two decades after infection. Symptoms first appear in many patients with chronic hepatitis C at the time of development of advanced liver disease.

In chronic hepatitis, inflammatory cells infiltrate the portal tracts and may also collect in small clusters in the parenchyma. The latter instance is usually accompanied by focal liver cell necrosis. The margin of the parenchyma and portal tracts may become inflamed, with liver cell necrosis at this site (interface hepatitis). If and when the disease progresses, the inflammation and liver cell death may lead to fibrosis. Mild fibrosis is confined to the portal tracts and immediately adjacent parenchyma. More severe fibrosis leads to bridging between portal tracts and between portal tracts and hepatic veins. Such fibrosis can progress to cirrhosis, defined as a state of diffuse fibrosis in which fibrous septae separate clusters of liver cells into nodules. The extent of fibrosis determines the stage of disease and can be reliably assessed. Severe fibrosis and necroinflammatory changes predict progression to cirrhosis. Once cirrhosis is established, complications can ensue that are secondary to liver failure and/or to portal hypertension, such as jaundice, ascites, variceal hemorrhage, and encephalopathy. The development of any of these complications marks the transition from a compensated to a decompensated cirrhosis.

Chronic hepatitis C infection leads to cirrhosis in at least 20 percent of patients within 2 decades of the onset of infection. Cirrhosis and end-stage liver disease may occasionally develop rapidly, especially among patients with concomitant alcohol use. Chronic infection by HCV is associated with an increased risk of liver cancer. The prevailing concept is that hepatocellular carcinoma (HCC) occurs against a background of inflammation and regeneration associated with chronic hepatitis over the course of approximately 3 or more decades. Most cases of HCV-related HCC occur in the presence of cirrhosis.

Liver fibrosis is one of the processes that occurs when the liver is damaged. Such damage may be the result of viral activity (e.g., chronic hepatitis types B or C) or other liver infections (e.g., parasites, bacteria); chemicals (e.g., pharmaceuticals, recreational drugs, excessive alcohol, exposure to pollutants); immune processes (e.g., autoimmune hepatitis); metabolic disorders (e.g., lipid, glycogen, or metal storage disorders); or cancer growth (primary or secondary liver cancer). Fibrosis is both a sign of liver damage and a potential contributor to liver failure via progressive cirrhosis of the liver.

It has been disclosed that the inhibition of the family of TGFβ kinases is useful in the treatment of fibroproliferative disorders, including liver fibrosis. However, as it is noted above, liver fibrosis may be caused by different ethiological agents, including the Hepatitis C virus. Most importantly, liver fibrosis is a specific condition in the disease progression of patients infected with HCV.

It has been surprisingly found that the compounds of the present invention inhibit HCV replication. HCV replication refers to the process of reproducing or making copies of HCV RNA. In the present invention HCV replication both refers to the replication of the HCV virus as a whole or the replication of the HCV RNA genome.

It is important to treat HCV infected patients at early stages in order to avoid disease progression, thereby avoiding that the patient develops chronic hepatitis, liver fibrosis, cirrhosis, hepatocellular carcinoma (HCC), or death.

In addition, the compounds of the invention are valuable in that they may diminish the HCV viral load of a patient to undetected levels.

DESCRIPTION OF THE DRAWINGS

FIG. 1 illustrates the mean plasma and tissue concentrations (n=3) of compound nr. 21 after a single oral administration at 20 mg base-eq./kg in the male Swiss SPF (CD1)-mice.

DISCLOSURE OF THE INVENTION

The present invention thus relates to the use of a compound of the formula (I) for the manufacture of a medicament useful for inhibiting HCV activity in a mammal infected with HCV. Said compound is a pteridine of the formula (I):

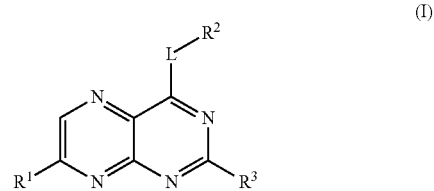

an N-oxide, salt, stereoisomeric form, racemic mixture, prodrug, ester or metabolite thereof, wherein $R^1$ is independently hydrogen, amino, mono- or disubstituted amino, wherein the substituent(s) of the amino may be selected from $C_{1-6}$alkyl, $C_{2-6}$alkenyl, $C_{2-6}$alkynyl, $C_{1-4}$alkoxy$C_{1-4}$alkyl, di$C_{1-4}$alkylamino$C_{1-4}$alkyl, piperidin-1-yl-$C_{1-4}$alkyl, aryl$C_{1-6}$alkyl, wherein the aryl group may be further substituted with $C_{1-4}$alkyl, or $C_{1-4}$alkoxy;

L is —$NR^8$—, —$NR^8$—$C_{1-6}$alkanediyl-, —$NR^8$—CO—$C_{1-6}$alkanediyl-, —$NR^8$—$SO_2$—$C_{1-6}$alkanediyl-, —O—, —O—$C_{1-6}$alkanediyl-, —O—CO—, —O—CO—$C_{1-6}$alkanediyl-, —S—, —S—$C_{1-6}$alkanediyl-, or

wherein the dotted ring together with N and Z form a $Het^1$ cycle having 5 to 8 members including ring members N and Z, and wherein said L ring is attached to the pteridine ring by the nitrogen atom;

Z represents N or CH;

$R^2$ represents hydrogen, hydroxy$C_{1-6}$alkyl, $C_{3-7}$cycloalkyl, aryl, $Het^1$, or $Het^2$, wherein said $C_{3-7}$cycloalkyl, aryl, $Het^1$, and $Het^2$ are each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, and aminophenylcarbonyl, and wherein the $C_{1-4}$alkyl may be further substituted with —$COOR^7$;

$R^3$ represents a $C_{1-6}$alkyl, $C_{3-7}$cycloalkyl, aryl, aryl$C_{1-6}$alkyl, $Het^1$, $Het^2$ or $Het^2$-$C_{1-6}$alkyl, each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}COOR^7$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$; and wherein $R^{4a}$ and $R^{4b}$ may optionally form, together with the nitrogen atom to which they are bound, a 5 to 8 membered saturated, unsaturated or partially unsaturated ring, optionally comprising one or two additional heteroatoms;

each $R^{4a}$ and $R^{4b}$ is independently hydrogen, $C_{1-4}$alkyl, hydroxy$C_{1-4}$alkyl, $Het^1$-$C_{1-4}$alkyl, polyhalo$C_{1-4}$alkyl, cyano, or nitro;

each $R^5$ is independently hydrogen, or $C_{1-4}$alkyl;
each $R^6$ is independently hydrogen, or $C_{1-4}$alkyl;
each $R^7$ is independently hydrogen, or $C_{1-4}$alkyl; and
$R^8$ is hydrogen, $C_{1-10}$alkyl, $C_{2-10}$alkenyl, $C_{2-10}$alkynyl, $C_{1-10}$alkylcarbonyl, amino-$C_{1-10}$alkyl, aryl, arylcarbonyl, aryl$C_{1-10}$alkyl, $Het^1$, $Het^1C_{1-6}$alkyl, or a protecting group, wherein the aryl is optionally substituted with 1 to 3 substituents selected from $C_{1-4}$alkyl, $C_{2-4}$alkenyl, $C_{2-4}$alkynyl, $C_{1-4}$alkylcarbonyl, phenyl, $C_{1-4}$alkylphenyl, phenylcarbonyl, aminophenyl, amino$C_{1-4}$alkylphenyl, aminophenylcarbonyl, halo, —$OR^6$, —$NR^{4a}R^{4b}$, —$SR^5$, —$SOR^5$, —$NR^{4a}SOR^5$, —$NR^{4a}SO_2R^5$, —$SO_2R^5$, —$OCOR^6$, —$NR^{4a}COR^6$, —$NR^{4a}CONR^{4a}R^{4b}$, —$NR^{4a}COOR^6$, —$OCONR^{4a}R^{4b}$, —$COOR^6$, —$SO_3R^6$, —$CONR^{4a}R^{4b}$, —$SO_2NR^{4a}R^{4b}$, cyano, polyhalo-$C_{1-4}$alkyl, and nitro;

$Het^1$ as a group or part of a group is defined as a saturated or partially unsaturated monocyclic, bicyclic or tricyclic heterocycle having preferably 3 to 12 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkoxy, halo, hydroxy, oxo, optionally mono- or disubstituted amino, nitro, cyano, polyhalo$C_{1-4}$alkyl, carboxyl, $C_{1-6}$alkoxy-carbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are hydrogen, or $C_{1-4}$alkyl;

$Het^2$ as a group or part of a group is defined as an aromatic monocyclic, bicyclic or tricyclic heterocycle having 3 to 14 ring members, preferably 5 to 10 ring members and more preferably 5 to 6 ring members, which contains one or more heteroatom ring members each independently selected from nitrogen, oxygen or sulfur, and which is optionally substituted on one or more carbon atoms by $C_{1-6}$alkyl, optionally mono- or disubstituted amino$C_{1-6}$alkyl, hydroxy$C_{1-6}$alkyl, $C_{1-6}$alkoxy, halo, hydroxy, optionally mono- or disubstituted amino, nitro, cyano, polyhalo-$C_{1-4}$alkyl, carboxyl, $C_{1-6}$alkoxycarbonyl, $C_{3-7}$cycloalkyl, optionally mono- or disubstituted aminocarbonyl, methylthio, methylsulfonyl, aryl, $Het^1$ and an aromatic monocyclic, bicyclic or tricyclic heterocycle having 3 to 12 ring members; whereby the optional substituents on any amino function are hydrogen, or $C_{1-4}$alkyl; and aryl as a group or part of a group is phenyl.

The present invention further relates to the use of a compound of the formula (II) for the manufacture of a medicament useful for inhibiting HCV activity in a mammal infected with HCV. Said compound is a pteridine of the formula (II):

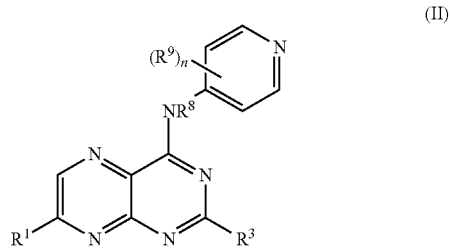

(II)

an N-oxide, salt, stereoisomeric form, racemic mixture, prodrug, ester or metabolite thereof, wherein $R^1$, $R^3$, $R^{4a}$, $R^{4b}$, $R^5$, $R^6$, $R^7$, $R^8$, $Het^1$, and $Het^2$ have the meaning as indicated above; wherein $R^9$ represents $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, or aminophenyl-carbonyl, and wherein the $C_{1-4}$alkyl may be further substituted with —$COOR^7$; and n is 0, 1, 2, 3, or 4.

The present invention further relates to the use of a compound of the formula (III) for the manufacture of a medicament useful for inhibiting HCV activity in a mammal infected with HCV. Said compound is a pteridine of the formula (III):

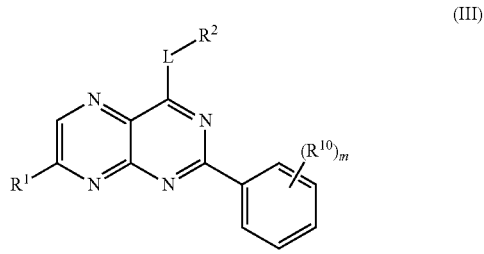

(III)

an N-oxide, salt, stereoisomeric form, racemic mixture, prodrug, ester or metabolite thereof, wherein $R^1$, L, $R^2$, $R^{4a}$, $R^{4b}$, $R^5$, $R^6$, $R^7$, $R^8$, $Het^1$, and $Het^2$ have the meaning as indicated above; wherein $R^{10}$ represents $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}COOR^7$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, and —$SO_2NR^{4a}R^{4b}$; and m is 0, 1, 2, 3, or 4.

The present invention further relates to the use of a compound of the formula (IV) for the manufacture of a medicament useful for inhibiting HCV activity in a mammal infected with HCV. Said compound is a pteridine of the formula (IV):

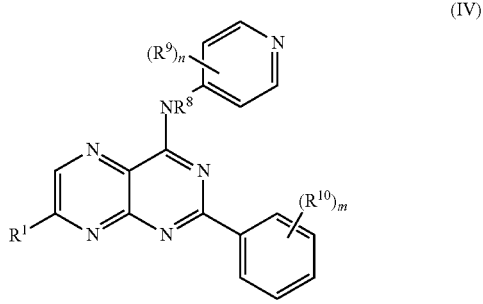

(IV)

an N-oxide, salt, stereoisomeric form, racemic mixture, prodrug, ester or metabolite thereof, wherein $R^1$, $R^{4a}$, $R^{4b}$, $R^5$, $R^6$, $R^7$, $R^8$, $Het^1$, and $Het^2$ have the meaning as indicated above; wherein $R^9$ represents $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, or aminophenyl-carbonyl, and wherein the $C_{1-4}$alkyl may be further substituted with —$COOR^7$;

$R^{10}$ represents $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}COOR^7$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, and —$SO_2NR^{4a}R^{4b}$;

n is 0, 1, 2, 3, or 4; and
m is 0, 1, 2, 3, or 4.

The present invention further relates to the use of a compound of the formula (V) for the manufacture of a medicament useful for inhibiting HCV activity in a mammal infected with HCV. Said compounds are pteridines of the formula (V):

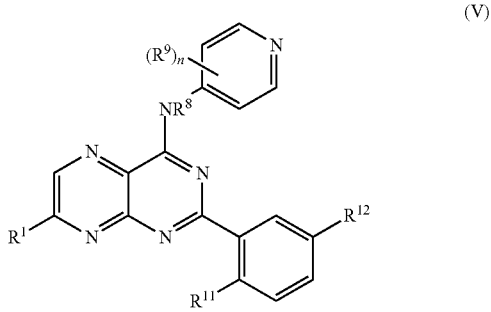

(V)

a salt, stereoisomeric form, and racemic mixture thereof, wherein $R^1$ is hydrogen or amino;

$R^8$ is hydrogen, $C_{1-6}$alkyl, amino$C_{1-4}$alkyl, phenyl$C_{1-4}$alkyl, pyrrolidin-1-yl$C_{1-4}$alkyl, or $C_{1-6}$alkoxycarbonyl;

each $R^9$ represents, independently, hydrogen, $C_{1-4}$alkyl, —$COR^6$, —$COOR^7$, or —$CONR^{4a}R^{4b}$;

n is 0, 1, 2, 3, or 4;

$R^{11}$ represents hydrogen, halo, or —$NR^{4a}R^{4b}$, wherein $R^{4a}$ and $R^{4b}$ may optionally form, together with the nitrogen atom to which they are bound, a 5 to 8 membered saturated, unsaturated or partially unsaturated ring, optionally comprising one or two additional heteroatoms;

$R^{12}$ represents hydrogen, halo, $C_{1-4}$alkyl, or polyhalo$C_{1-4}$alkyl;

$R^6$ is hydrogen, or $C_{1-4}$alkyl;

$R^7$ is hydrogen, or $C_{1-4}$alkyl; and $R^{4a}$ and $R^{4b}$, independently, are hydrogen, $C_{1-4}$alkyl, 2-oxo-pyrrolidin-1-yl-$C_{1-4}$alkyl.

One embodiment relates to the use of the compounds of formulae (II), (IV), or (V) as specified above, wherein n is 1.

In a further aspect the invention relates to a method of inhibiting HCV replication in a mammal infected with HCV, said method comprising the administration of an HCV inhibitory effective amount of a compound of formulae (I), (II), (III), (IV), or (V) as specified above or as further specified hereinafter. In a particular embodiment, the method of inhibiting HCV replication in a mammal infected with HCV comprises the administration of an HCV inhibitory effective amount of a compound of formulae (II), (IV), or (V) wherein n is 1.

In a further aspect the invention relates to a method of treating a mammal infected with HCV, said method comprising the administration of an HCV inhibitory effective amount of a compound of formulae (I), (II), (III), (IV), or (V) as specified above or as further specified hereinafter. In a particular embodiment, the method of treating a mammal infected with HCV comprises the administration of an HCV inhibitory effective amount of a compound of formulae (II), (IV), or (V) wherein n is 1.

In a further embodiment, the present invention relates to the use of a compound of the formula (VI) for the manufacture of a medicament for inhibiting HCV replication in a mammal infected with HCV. Said compound is a pteridine of the formula (VI):

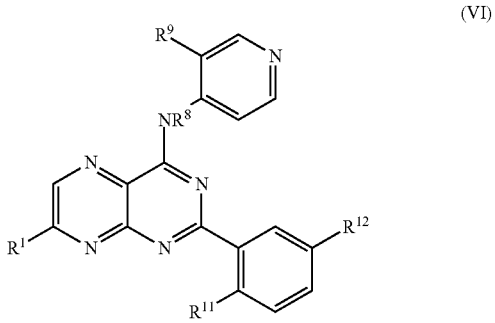

(VI)

a salt, stereoisomeric form, and racemic mixture thereof, wherein $R^1$, $R^8$, $R^9$, $R^{11}$, $R^{12}$, $R^6$ are as defined above.

In a further embodiment the invention relates to a method of inhibiting HCV replication in a mammal infected with HCV, said method comprising the administration of an HCV inhibitory effective amount of a compound of formula (VI) as specified above or as further specified hereinafter.

In a further embodiment the invention relates to a method of treating a mammal infected with HCV, said method comprising the administration of an HCV inhibitory effective amount of a compound of formula (VI) as specified above or as further specified hereinafter.

Still further embodiments of the invention relate to the use of the compounds of the formulae (V) or (VI) for the manufacture of a medicament for inhibiting HCV replication in a mammal infected with HCV. Said compounds are pteridines of the formulae (V) or (VI) wherein, where applicable n is 1, and $R^1$ is hydrogen or amino;
$R^8$ is hydrogen, $C_{1-6}$alkyl, phenyl$C_{1-4}$alkyl;
$R^9$ represents hydrogen, $C_{1-4}$alkyl, —COR$^6$, —COOR$^7$, or —CONR$^{4a}R^{4b}$;
$R^{11}$ represents hydrogen, fluoro, or pyrrolidin-1-yl;
$R^{12}$ represents halo, $C_{1-4}$alkyl, or polyhalo$C_{1-4}$alkyl;
$R^6$ is hydrogen, or $C_{1-4}$alkyl;
$R^7$ is hydrogen, or $C_{1-4}$alkyl; and
$R^{4a}$ and $R^{4b}$, independently, are hydrogen, $C_{1-4}$alkyl, 2-oxo-pyrrolidin-1-yl-$C_{1-4}$alkyl.

Further embodiments of the invention relate to the method of inhibiting HCV replication in a mammal infected with HCV, and to the method of treating a mammal infected with HCV, said methods comprising the administration of an HCV inhibitory effective amount of a compound of formulae (V) or (VI) wherein, where applicable n is 1, and $R^1$, $R^8$, $R^9$, $R^{11}$, $R^{12}$ are as defined in the previous paragraph.

Yet still further embodiments of the invention relate to the use of the compounds of the formulae (V) or (VI) for the manufacture of a medicament for inhibiting HCV replication in a mammal infected with HCV. Said compounds are pteridines of the formulae (V) or (VI) wherein, where applicable n is 1, and $R^1$ is hydrogen;
$R^8$ is hydrogen, $C_{1-6}$alkyl, phenyl$C_{1-4}$alkyl;
$R^9$ represents hydrogen, $C_{1-4}$alkyl, or —COOR$^7$;
$R^{11}$ represents fluoro, or pyrrolidin-1-yl;
$R^{12}$ represents halo, or $C_{1-4}$alkyl; and
$R^7$ is hydrogen, or $C_{1-4}$alkyl.

Thus, further embodiments of the invention relate to a method of inhibiting HCV replication in a mammal infected with HCV, and to a method of treating a mammal infected with HCV, said methods comprising the administration of an HCV inhibitory effective amount of a compound of formulae (V) or (VI) wherein, where applicable n is 1, and $R^{11}$, $R^8$, $R^9$, $R^{11}$, $R^{12}$ are as defined in the previous paragraph.

In a further embodiment, the present invention relates to a pteridine of the formula (VII):

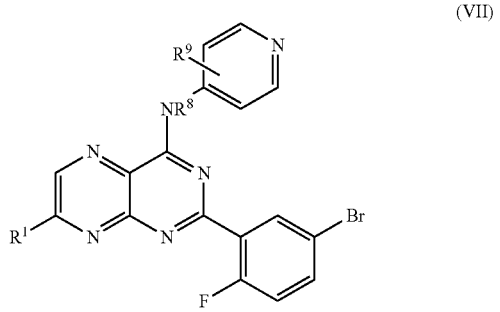

(VII)

a salt, stereoisomeric form, and racemic mixture thereof, wherein
$R^1$ is hydrogen or amino;
$R^8$ is hydrogen, $C_{1-6}$alkyl, phenyl$C_{1-4}$alkyl;
$R^9$ represents hydrogen, $C_{1-4}$alkyl, —COR$^6$, COOR$^7$, or —CONR$^{4a}R^{4b}$;
$R^6$ is independently hydrogen, or $C_{1-4}$alkyl;
each $R^7$ is independently hydrogen, or $C_{1-4}$alkyl; and
each $R^{4a}$ and $R^{4b}$ is independently hydrogen, $C_{1-4}$alkyl, 2-oxo-pyrrolidin-1-yl-$C_{1-4}$alkyl;
with the proviso that when $R^8$ is hydrogen, $R^9$ is not hydrogen.

In a further embodiment, the present invention relates to a pteridine of the formula (VII), a salt, stereoisomeric form, and racemic mixture thereof, wherein
$R^8$ is $C_{1-6}$alkyl, phenyl$C_{1-4}$alkyl;
$R^1$, $R^{4a}$, $R^{4b}$, $R^6$, $R^7$, and $R^9$ are as recited in the previous paragraph.

In a further embodiment, the present invention relates to a pteridine of the formula (VII), a salt, stereoisomeric form, and racemic mixture thereof, wherein
$R^9$ represents $C_{1-4}$alkyl, —COR$^6$, COOR$^7$, or —CONR$^{4a}R^{4b}$;
$R^1$, $R^{4a}$, $R^{4b}$, $R^6$, $R^7$, and $R^8$ are as recited in the second previous paragraph.

In a further embodiment, the present invention relates to a pteridine of the formula (VIII):

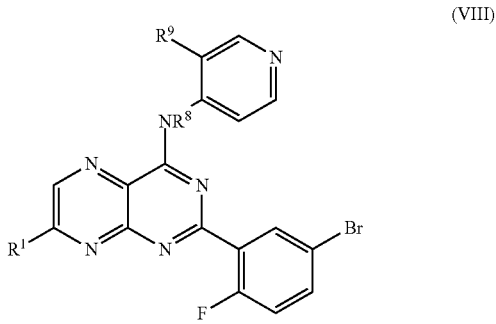

(VIII)

a salt, stereoisomeric form, and racemic mixture thereof, wherein
$R^1$ is independently hydrogen or amino;
$R^8$ is hydrogen, $C_{1-6}$alkyl, phenyl$C_{1-4}$alkyl;
$R^9$ represents hydrogen, $C_{1-4}$alkyl, —COR$^6$, COOR$^7$, or —CONR$^{4a}R^{4b}$;
$R^6$ is independently hydrogen, or $C_{1-4}$alkyl;
each $R^7$ is independently hydrogen, or $C_{1-4}$alkyl; and
each $R^{4a}$ and $R^{4b}$ is independently hydrogen, $C_{1-4}$alkyl, 2-oxo-pyrrolidin-1-yl-$C_{1-4}$alkyl;
with the proviso that when $R^8$ is hydrogen, $R^9$ is not hydrogen.

In a further embodiment, the present invention relates to a pteridine of the formula (VIII), a salt, stereoisomeric form, and racemic mixture thereof, wherein
$R^9$ represents $C_{1-4}$alkyl, —COR$^6$, COOR$^7$, or —CONR$^{4a}R^{4b}$;
—$R^1$, $R^{4a}$, $R^{4b}$, $R^6$, $R^7$, and $R^8$ are as recited in the previous paragraph.

In a further embodiment, the present invention relates to a pteridine of the formula (VIII), a salt, stereoisomeric form, and racemic mixture thereof, wherein
$R^8$ is $C_{1-6}$alkyl, phenyl$C_{1-4}$alkyl;
$R^1$, $R^{4a}$, $R^{4b}$, $R^6$, $R^7$, and $R^9$ are as recited in the second previous paragraph.

In a further embodiment, the present invention relates to a pteridine of the formula (VII) or (VIII) as set forth above, wherein
$R^1$ is hydrogen;
$R^8$ is hydrogen;
$R^9$ represents $C_{1-4}$alkyl.

In a further embodiment, the present invention relates to a pteridine of the formula (VII) or (VIII) as set forth above, wherein $R^1$ is hydrogen;
$R^8$ is $C_{1-6}$alkyl;
$R^9$ represents hydrogen.

A method of treating clinical conditions relating to HCV infection in a mammal, said method comprising the administration of an HCV inhibitory effective amount of a compound of formula (V) wherein $R^1$, $R^8$, $R^9$, $R^{11}$, $R^{12}$ are as defined hereinafter.

A method as in the previous paragraph wherein the clinical conditions are other than liver fibrosis.

The compounds of formulae (I), (II), (III), (IV), (V), (VI), (VII), and (VIII) show activity against the HCV virus and are therefore useful as a medicament, and in the manufacture of a medicament for preventing, treating or combating infection, clinical conditions, or a disease associated with HCV infection.

The compounds of formulae (I), (II), (III), (IV), (V), (VI), (VII), and (VIII) show activity against the HCV virus and are therefore useful as a medicament, and in the manufacture of a medicament for preventing, treating or combating clinical conditions associated with HCV infection other than liver fibrosis.

The term "$C_{1-2}$alkyl" as a group or part of a group defines straight and branched chained saturated hydrocarbon radicals having from 1 to 2 carbon atoms, such as, for example, methyl, ethyl, and the like.

The term "$C_{1-4}$alkyl" as a group or part of a group defines straight and branched chained saturated hydrocarbon radicals having from 1 to 4 carbon atoms, such as, for example, the groups defined for $C_{1-2}$alkyl and propyl, butyl, 2-methylpropyl and the like.

The term "$C_{1-6}$alkyl" as a group or part of a group defines straight and branched chained saturated hydrocarbon radicals having from 1 to 6 carbon atoms such as, for example, the groups defined for $C_{1-4}$alkyl and pentyl, hexyl, 2-methylbutyl, 3-methylpentyl and the like.

The term "$C_{1-10}$alkyl" as a group or part of a group defines straight and branched chained saturated hydrocarbon radicals having from 1 to 10 carbon atoms such as, for example, the groups defined for $C_{1-6}$alkyl and heptyl, octyl, nonyl, decyl and the like.

The term "$C_{2-4}$alkenyl" as a group or part of a group defines straight and branched chained hydrocarbon radicals having saturated carbon-carbon bonds and at least one double bond, and having from 2 to 4 carbon atoms, such as, for example, ethenyl, prop-1-enyl, but-1-enyl, but-2-enyl, and the like. Preferred are $C_{2-4}$alkenyls having one double bond.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, the groups defined for $C_{2-4}$alkenyl and pent-1-enyl, pent-2-enyl, hex-1-enyl, hex-2-enyl, hex-3-enyl, 1-methyl-pent-2-enyl and the like. Preferred are $C_{2-6}$alkenyls having one double bond.

The term "$C_{2-10}$alkenyl" as a group or part of a group defines straight and branched chained hydrocarbon radicals having saturated carbon-carbon bonds and at least one double bond, and having from 2 to 10 carbon atoms, such as, for example, the groups defined for $C_{2-6}$alkenyl and hept-1-enyl, hept-2-enyl, 2-methyl-hept-1-enyl, oct-3-enyl, non-4-enyl, 1-methyl-non-2-enyl and the like. Preferred are $C_{2-10}$alkenyls having one double bond.

The term "$C_{2-4}$alkynyl" as a group or part of a group defines straight and branched chained hydrocarbon radicals having saturated carbon-carbon bonds and at least one triple bond, and having from 2 to 4 carbon atoms, such as, for example, ethynyl, prop-1-ynyl, but-1-ynyl, but-2-ynyl, and the like. Preferred are $C_{2-4}$alkynyls having one triple bond.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, the groups defined for $C_{2-4}$alkynyl and pent-1-ynyl, pent-2-ynyl, hex-1-ynyl, hex-2-ynyl, hex-3-ynyl, 1-methyl-pent-2-ynyl, pent-2-en-4-ynyl and the like. Preferred are $C_{2-6}$alkynyls having one triple bond.

The term "$C_{2-10}$alkynyl" as a group or part of a group defines straight and branched chained hydrocarbon radicals having saturated carbon-carbon bonds and at least one triple bond, and having from 2 to 10 carbon atoms, such as, for example, the groups defined for $C_{2-6}$alkynyl and hept-1-ynyl, hept-2-ynyl, 2-methyl-hept-1-ynyl, oct-3-ynyl, non-4-ynyl, 1-methyl-non-2-ynyl and the like. Preferred are $C_{2-10}$alkynyls having one triple bond.

The term "$C_{1-6}$alkanediyl" as a group or part of a group defines bivalent straight and branched chained hydrocarbons having from 1 to 6 carbon atoms such as, for example, methanediyl, 1,2-ethanediyl, or 1,1-ethanediyl, 1,3-propanediyl, 1,3-butanediyl, 1,4-butanediyl, 1,3-pentanediyl, 1,5-pentanediyl, 1,4-hexanediyl, 1,6-hexanediyl, and the like.

The term "$C_{3-7}$cycloalkyl" is generic to cyclopropyl, cyclobutyl, cyclopentyl, cyclohexyl and cycloheptyl.

The term "aryl" as a group or part of a group is meant to include phenyl or naphtyl. In a preferred embodiment, the term "aryl" as a group or part of a group is phenyl.

The term "halo" is generic to fluoro, chloro, bromo or iodo.

As used in the foregoing and hereinafter "polyhalo$C_{1-4}$alkyl" as a group or part of a group is defined as mono- or polyhalosubstituted $C_{1-4}$alkyl, for example, 1,1,1-trifluoroethyl, 1,1-difluoro-ethyl, the polyhalomethyl groups mentioned hereinafter, and the like. A preferred subgroup of polyhalo$C_{1-4}$alkyl is polyhalomethyl, wherein the latter as a group or part of a group is defined as mono- or polyhalo-substituted methyl, in particular methyl with one or more fluoro atoms, for example, difluoromethyl or trifluoromethyl. In case more than one halogen atom is attached to an alkyl group within the definition of polyhalomethyl or polyhalo$C_{1-4}$alkyl, they may be the same or different.

The term "protecting group" refers to an amino-protecting group such as such as $C_{1-10}$alkoxy-carbonyl, aryl$C_{1-10}$alkoxy-carbonyl, like benzoyl, anisoyl-, isobutyroyl-, acetyl-, or tert-butylbenzoyl (Breipohl et al. (1997) Tetrahedron 53, 14671-14686). The protecting group may be as well an acid-labile protecting group such as dimethoxytrityl.

It should also be noted that the radical positions on any molecular moiety used in the definitions, unless indicated otherwise, may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

When any variable (e.g. halogen or $C_{1-4}$alkyl) occurs more than one time in any constituent, each definition is independent.

The N-oxide forms of the present compounds are meant to comprise any one of the compounds of the present invention wherein one or several nitrogen atoms are oxidized to the so-called N-oxide.

For therapeutic use, the salts of the compounds of the present invention are those wherein the counter-ion is pharmaceutically or physiologically acceptable. However, salts having a pharmaceutically unacceptable counter-ion may also find use, for example, in the preparation or purification of a pharmaceutically acceptable compound of the present invention. All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecyl-sulphuric, heptanoic, hexanoic, benzoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of the present invention containing an acidic proton may also be converted into their non-toxic metal or amine addition base salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Alternatively, when a carboxyl moiety is present on a compound of the present invention, the compound may also be supplied as a salt with a pharmaceutically acceptable cation.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

In the event that any of the substituents of the compounds of the present invention contain chiral centers, as some, indeed, do, the compounds the present invention include all stereoisomeric forms thereof, both as isolated stereoisomers and mixtures of these stereoisomeric forms.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of the present invention can be obtained separately by conventional methods. Appropriate physical separation methods that may advantageously be employed are, for example, selective crystallization and chromatography, e.g. column chromatography.

The present compounds may also exist in their tautomeric forms. Such forms, although not explicitly indicated in the above formula are intended to be included within the scope of the present invention. For example, within the definition of Het$^2$, for example an 1,2,4-oxadiazole may be substituted with a hydroxy or a mercapto group in the 5-position, thus being in equilibrium with its respective tautomeric form as depicted below.

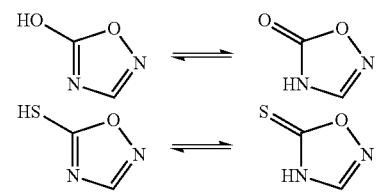

The term "prodrug" as used throughout this text means the pharmacologically acceptable derivatives such as esters, amides and phosphates, such that the resulting in vivo biotransformation product of the derivative is the active drug as defined in the compounds of the present invention. The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either by routine manipulation or in vivo, to the parent compound. For example, a substituent containing sulfhydryl could be coupled to a carrier which renders the compound biologically inactive until removed by endogenous enzymes or, for example, by enzymes targeted to a particular receptor or location in the subject.

Prodrugs are characterized by excellent aqueous solubility, increased bioavailability and are readily metabolized into the active inhibitors in vivo.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", "compounds of formula (II)", "compounds of formula (III)", "compounds of formula (IV)", "compounds of formula (V)", "compounds of formula (VI)", "compounds of formula (VII)", "compounds of formula (VIII)", "compounds of formulas (V) to (VIII)", or "the compounds of present invention" or similar term is meant to include the compounds of general formulas (I), (II), (III), (IV), (V), (VI), (VII), (VIII), their N-oxides, salts, stereoisomeric forms, racemic mixtures, prodrugs, esters and metabolites, as well as their quaternized nitrogen analogues. An interesting subgroup of the compounds of formula (V) or any subgroup thereof are the N-oxides, salts and all the stereoisomeric forms of the compounds of formula (V).

Embodiments of the present invention are those compounds of the present invention or any of the subgroups thereof wherein the 4-pyridyl forms a N-oxide, for example the N-oxide of compound nr. 24.

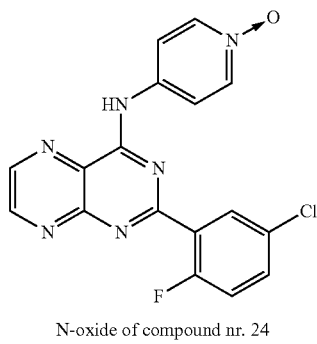 [SMILES: [O-][n+]1ccc(Nc2nc(-c3cc(Cl)ccc3F)nc3nccnc23)cc1]

N-oxide of compound nr. 24

Further embodiments of the present invention are those compounds of the present invention or any of the subgroups of compounds of the present invention wherein the compound occurs as an acid-addition salt, wherein the salt preferably is selected from hydrochloride, hydrobromide, trifluoroacetate, fumarate, chloroacetate, methanesulfonate, oxalate, acetate and citrate.

Further embodiments of the present invention are those compounds of the present invention or any subgroup thereof wherein $R^1$ is independently hydrogen, amino, mono- or disubstituted amino, wherein the substituent(s) of the amino may be selected from $C_{1-6}$alkyl, $C_{1-4}$alkoxy$C_{1-4}$alkyl, di-$C_{1-4}$alkylamino$C_{1-4}$alkyl, piperidin-1-yl-$C_{1-4}$alkyl, aryl$C_{1-6}$alkyl, wherein the aryl group may be further substituted with $C_{1-4}$alkyl, or $C_{1-4}$alkoxy.

Further embodiments of the present invention are those compounds of the present invention or any subgroup thereof wherein $R^1$ is independently hydrogen, amino, mono- or disubstituted amino, wherein the substituent(s) of the amino may be selected from $C_{1-4}$alkyl, $C_{1-4}$alkoxy$C_{1-4}$alkyl, di-$C_{1-4}$alkylamino$C_{1-4}$alkyl, piperidin-1-yl-$C_{1-4}$alkyl, aryl$C_{1-6}$alkyl, wherein the aryl group may be further substituted with $C_{1-4}$alkoxy.

Further embodiments of the present invention are those compounds of the present invention or any subgroup thereof wherein $R^1$ is independently hydrogen, amino, mono- or disubstituted amino, wherein the substituent(s) of the amino may be selected from $C_{1-2}$alkyl, $C_{1-2}$alkoxy$C_{1-2}$alkyl, di-$C_{1-2}$alkylamino$C_{1-2}$alkyl, piperidin-1-yl-$C_{1-2}$alkyl, aryl$C_{1-2}$alkyl, wherein the aryl group may be further substituted with $C_{1-2}$alkoxy.

Further embodiments of the present invention are those compounds of the present invention or any subgroup thereof wherein $R^1$ is independently hydrogen, amino, mono- or disubstituted amino, wherein the substituent(s) of the amino may be selected from methyl, methoxyethyl, dimethylaminoethyl, piperidin-1-ylethyl, benzyl, wherein the phenyl group may be further substituted with methoxy.

Further embodiments of the present invention are those compounds of the present invention or any subgroup thereof wherein $R^1$ is independently hydrogen, amino, or monosubstituted amino, wherein the substituent of the amino may be selected from methoxyethyl, dimethylaminoethyl, piperidin-1-ylethyl, and benzyl, wherein the phenyl group is further substituted with methoxy.

Further embodiments of the present invention are those compounds of the present invention or any subgroup thereof wherein $R^1$ is independently hydrogen or amino.

Further embodiments of the present invention are those compounds of the present invention or any subgroup thereof wherein $R^8$ is hydrogen, $C_{1-10}$alkyl, amino$C_{1-10}$alkyl, aryl-$C_{1-10}$alkyl, $Het^1C_{1-6}$alkyl, or a protecting group, wherein the aryl is optionally substituted with 1 to 3 substituents selected from $C_{1-4}$alkyl, $C_{1-4}$alkyl-carbonyl, halo, —$OR^6$, —$NR^{4a}R^{4b}$, —$SR^5$, and polyhalo$C_{1-4}$alkyl.

Further embodiments of the present invention are those compounds of the present invention or any subgroup thereof wherein $R^S$ is hydrogen, $C_{1-6}$alkyl, amino$C_{1-6}$alkyl, aryl$C_{1-6}$alkyl, $Het^1C_{1-6}$alkyl, or $C_{1-6}$alkoxy-carbonyl.

Further embodiments of the present invention are those compounds of formula compounds of the present invention or any subgroup thereof wherein $R^8$ is hydrogen, $C_{1-6}$alkyl, amino$C_{1-4}$alkyl, phenyl$C_{1-4}$alkyl, pyrrolidin-1-yl$C_{1-4}$alkyl, or $C_{1-6}$alkoxy-carbonyl.

Further embodiments of the present invention are those compounds of formula compounds of the present invention or any subgroup thereof wherein each $R^9$ represents, independently, hydrogen, $C_{1-4}$alkyl, polyhalo$C_{1-4}$alkyl, halo, —$COR^6$, —$COOR^7$, —$CONR^{4a}R^{4b}$, —$OR^7$, —$NR^{4a}R^{4b}$, —$NR^{4a}COR^6$, —$NR^{4a}SO_2R^5$, —$SR^5$, or morpholin-4-yl, and wherein the $C_{1-4}$alkyl may be further substituted with —$COOR^7$.

Further embodiments of the present invention are those compounds of the present invention or any subgroup thereof wherein each $R^9$ represents, independently, hydrogen, $C_{1-4}$alkyl, —$COR^6$, —$COOR^7$, or —$CONR^{4a}R^{4b}$, and wherein the $C_{1-4}$alkyl may be further substituted with —$COOR^7$.

Further embodiments of the present invention are those compounds of the present invention or any subgroup thereof wherein each $R^9$ represents, independently, hydrogen, $C_{1-4}$alkyl, —$COR^6$, —$COOR^7$, or —$CONR^{4a}R^{4b}$.

Further embodiments of the present invention are those compounds of formulae (V), (VI) or any of the subgroups thereof wherein $R^{11}$ represents hydrogen, fluoro, or pyrrolidin-1-yl.

Further embodiments of the present invention are those compounds of formulae (V), (VI) or any of the subgroups thereof wherein $R^{11}$ represents hydrogen or fluoro.

Further embodiments of the present invention are those compounds of formulae (V), (VI) or any of the subgroups thereof wherein $R^{12}$ represents halo, $C_{1-4}$alkyl, or polyhalo$C_{1-4}$alkyl.

Further embodiments of the present invention are those compounds of formulae (V), (VI) or any of the subgroups thereof wherein $R^{12}$ represents halo, or polyhalo$C_{1-4}$alkyl.

Further embodiments of the present invention are those compounds of formulae (V), (VI) or any of the subgroups thereof wherein $R^{12}$ represents chloro, bromo, fluoro, or trifluoromethyl.

Further embodiments of the present invention are those compounds of formulae (V), (VI) or any of the subgroups thereof wherein $R^{11}$ represents fluoro, and $R^{12}$ represents chloro, or bromo.

Further embodiments of the present invention are those compounds of formulae (V), (VI) or any of the subgroups thereof wherein $R^{11}$ represents hydrogen, and $R^{12}$ represents chloro, bromo, fluoro, or trifluoromethyl.

Compounds of particular interest are those compounds of formula (V) listed in Table 1 below, in particular compounds number 1, number 7, number 21, number 23, number 24, and number 25, and its N-oxides, salts and stereoisomers.

A number of synthetic routes may be employed to produce the compounds of the invention. In general, they may be synthesized using reactions known in the art. Any art-known method for synthesis may be employed. However, the following synthetic routes are convenient for preparation of the invention compounds.

The compounds of the formula (V) may be synthesized following a procedure adapted from Wamhoff, H.; Kroth, E. *Synthesis*, 1994, 405-410 as described in Scheme 1.

The 3-acylaminopyrazin-2-amides (1d) are then cyclized by the addition of a base to form pteridin-4-ol derivatives of formula (1e). The alcohol may then be replaced by a halogen with the help of a halogenating agent such as thionyl chloride in a suitable solvent like chloroform, dichloroethane or tetrahydrofuran (THF) in presence of a catalytic amount of dimethylformamide (DMF). Following, a nucleophilic substitution is performed on compound (1f) with an amine or an alcohol of formula HLR$^2$, together with a suitable base, such as TEA or DIPEA in an organic solvent such as DCM, THF or DMF, yielding the pteridine compounds of formula (1g).

Alternatively, the pteridin-4-ol may be converted in a one-pot procedure into the pteridines of formula (V) by reacting compounds of formula (1e) with an amine or alcohol of the formula HLR$^2$ together with a suitable base, such as TEA or DIPEA in the presence of benzotriazole-1-yl-oxy-tris-pyrrolidino-phosphonium hexafluoro-phosphate (PyBOP). In the formula HLR$^2$, H is hydrogen, and L and R$^2$ have the meanings indicated above in the definition of the substituents of compound of formula (V).

Scheme 2

Alternatively, the compounds of the formula (V) can be prepared from the corresponding pteridinones as starting materials followed by their conversion to the iminochlorides and the subsequent displacement of the chlorine atom with an appropriate amine such as a 4-aminopyridine as shown below in Scheme 2.

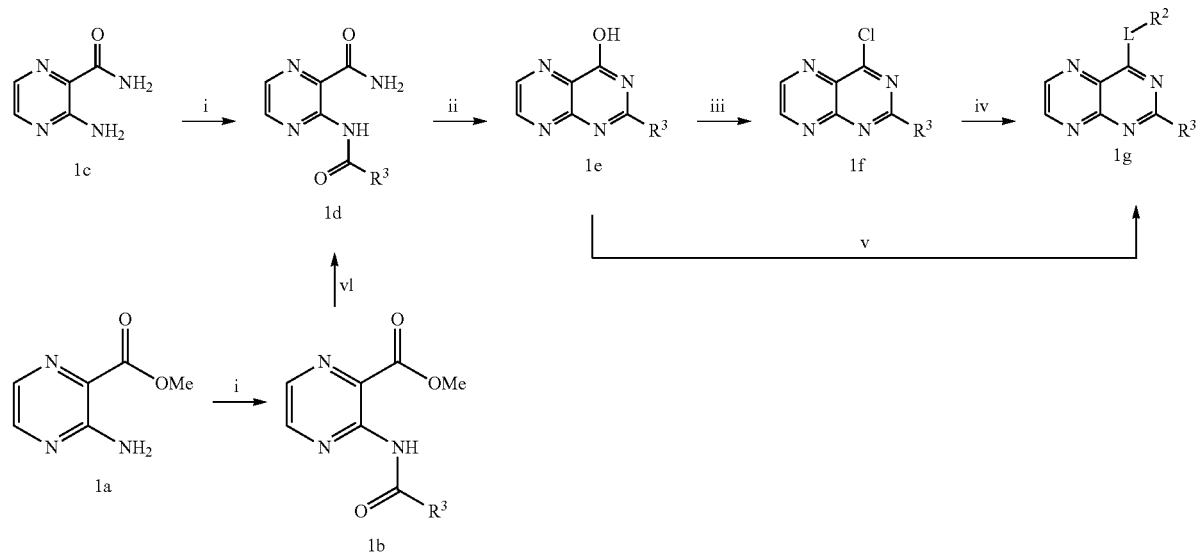

Basically, a methyl 3-amino-2-pyrazinecarboxylate (1a) is reacted with acylchloride in the presence of a suitable solvent such as chloroform or pyridine to afford 3-acylaminopyrazin-2-carboxylates (1b). Said 3-acylaminopyrazin-2-carboxylates (1b) are converted with for example ammonium hydroxide into 3-acylaminopyrazin-2-amides (1d). Optionally, 3-acylaminopyrazine-2-carboxamides (1d) may already be obtained by acylation of 3-amino-2-pyrazinecarboxamide (1c).

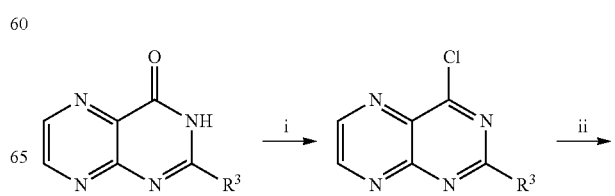

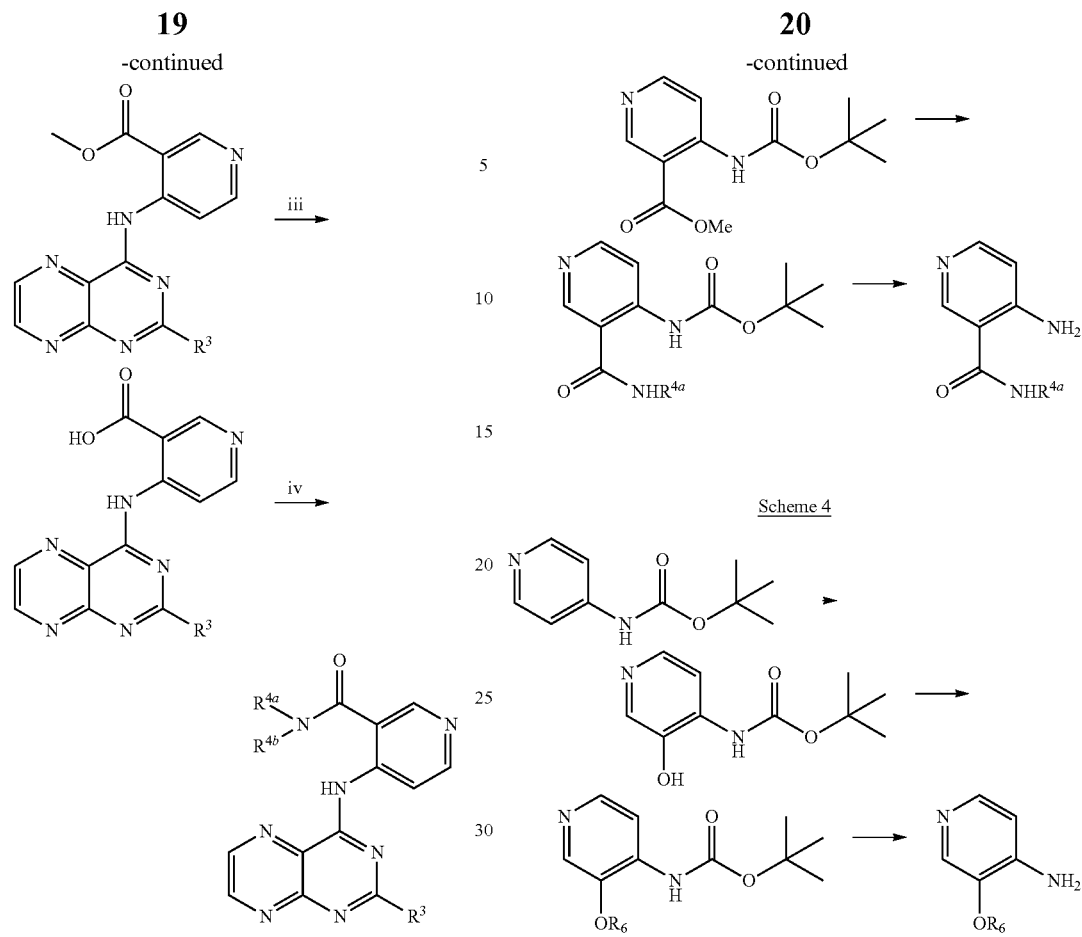

(i) thionyl chloride, DMF; (ii) 4-aminonicotinic acid methyl ester, TEA; (iii) NaOH; (iv) PyBOP, TEA, HNR$^{4a}$R$^{4b}$.

Schemes 3 and 4, shown below, provide alternative routes to pyridyl nucleus and further substitutions thereof.

Compounds embodied in the present invention are shown below in Table 1:

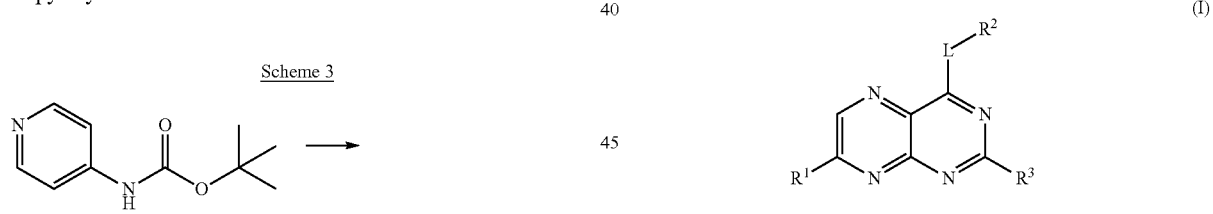

TABLE 1

| # | R$^1$ | L | R$^2$ | R$^3$ |
|---|---|---|---|---|
| 1 | H | —NH— | 4-pyridyl | 5-bromo-2-fluorophenyl |
| 2 | H | —N(CH$_3$)— | 4-pyridyl | 5-bromo-2-fluorophenyl |

TABLE 1-continued
| # | R¹ | L | R² | R³ |
|---|---|---|---|---|
| 3 | H | —N(CH$_2$CH$_2$CH$_2$CH$_3$)— | 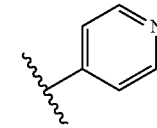 | 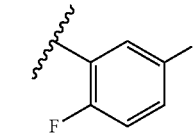 |
| 4 | H | —N[CH$_2$CH$_2$C(CH$_3$)$_3$]— | 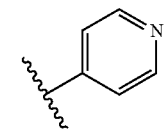 [SMILES: *c1ccncc1] | 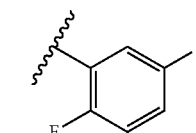 |
| 5 | H | —N(CH$_2$—Ph)— | 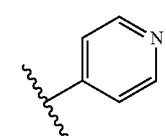 [SMILES: *c1ccncc1] | 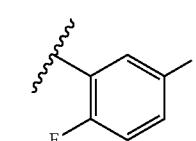 |
| 6 | H | —NH— | 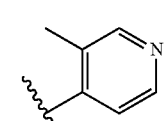 | 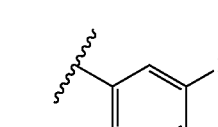 |
| 7 | H | —NH— | 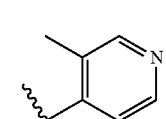 | 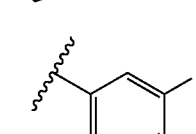 |
| 8 | H | —NH— | 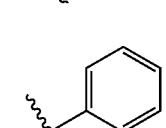 | 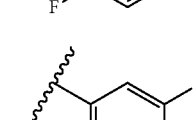 |
| 9 | H | —NH— | 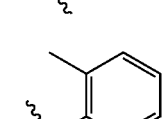 | 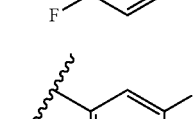 |
| 10 | H | —N(CH$_3$)— | 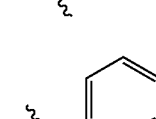 | 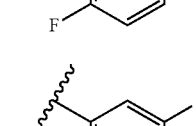 |
| 11 | H | —NH— | —CH$_2$—CH$_2$—OH | 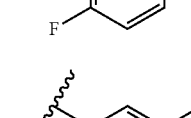 |
| 12 | H | 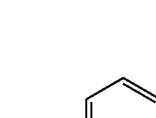 | 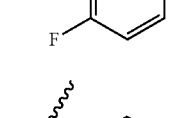 | |

TABLE 1-continued
| # | R¹ | L | R² | R³ |
|---|----|----|----|----|
| 13 | H | —NH— |  | 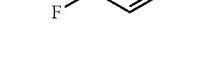 |
| 14 | H | —NH— |  | 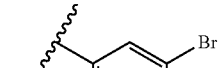 |
| 15 | H | —NH— | 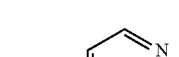 |  |
| 16 | H | —NH— |  |  |
| 17 | H | 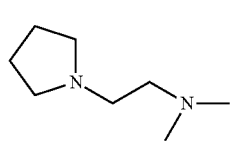 | 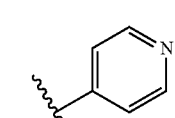 | 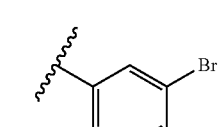 |
| 18 | H | —NH— | 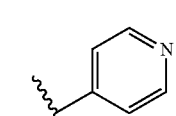 | 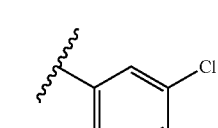 |
| 19 | H | —NH— | 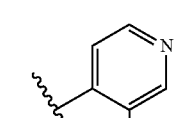 | 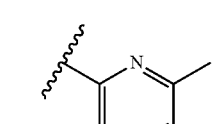 |
| 20 | H | —N(CH₂CH₂CH₂NH₂)— | 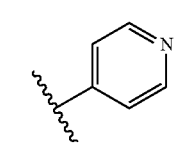 [SMILES: *c1ccncc1] | 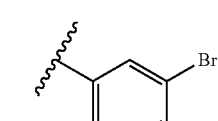 |
| 21 | H | —NH— | 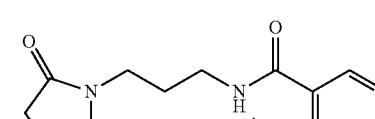 | 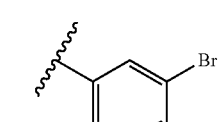 |

TABLE 1-continued

| # | R¹ | L | R² | R³ |
|---|---|---|---|---|
| 22 | H | phenethyl-N(CH₃)₂ | 4-pyridyl | 2-F, 5-Br phenyl |
| 23 | H | —NH— | 3-ethyl-4-pyridyl | 2-F, 5-Cl phenyl |
| 24 | H | —NH— | 4-pyridyl | 2-F, 5-Cl phenyl |
| 25 | H | —NH— | 3-methyl-4-pyridyl | 2-F, 5-Cl phenyl |
| 26 | H | —NH— | 4-pyridyl | 3-CF₃ phenyl |
| 27 | H | —NH— | 4-pyridyl | 3-F phenyl |

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will vary, however, depending on the conditions being treated and the judgment of the practitioner.

It should be noted that the compounds of the invention can be administered as individual active ingredients, or as mixtures of several embodiments of this formula. In addition, the compounds of the invention may be used as single therapeutic agents or in combination with other therapeutic agents.

Due to their favorable antiviral properties, as will be apparent from the examples, the compounds of the present invention are useful in the treatment of individuals infected by HCV and for the prophylaxis of these individuals. In general, the compounds of the present invention may be useful in the treatment of warm-blooded animals infected with flaviviruses. Conditions which may be prevented or treated with the compounds of the present invention, especially conditions associated with HCV and other pathogenic flaviviruses, such as Yellow fever, Dengue fever (types 1-4), St. Louis encephalitis, Japanese encephalitis, Murray valley encephalitis, West Nile virus and Kunjin virus. The conditions associated with HCV include progressive liver fibrosis, inflammation and necrosis leading to cirrhosis, end-stage liver disease, and HCC; and for the other pathogenic flaviruses the conditions include yellow fever, dengue fever, hemorraghic fever and encephalitis.

The compounds of the present invention or any subgroup thereof may therefore be used as medicines against the above-mentioned conditions. Said use as a medicine or method of treatment comprises the systemic administration to HCV-infected subjects of an amount effective to combat the conditions associated with HCV and other pathogenic flaviviruses. Consequently, the compounds of the present invention can be used in the manufacture of a medicament useful for treating conditions associated with HCV and other pathogenic flaviviruses.

In an embodiment, the invention relates to the use of a compound of formula (V) or any subgroup thereof as defined herein in the manufacture of a medicament for treating or combating infection or disease associated with HCV infection in a mammal. The invention also relates to a method of treating a flaviviral infection, or a disease associated with flavivirus infection comprising administering to a mammal in need thereof an effective amount of a compound of formula (V) or a subgroup thereof as defined herein.

In another embodiment, the present invention relates to the use of formula (V) or any subgroup thereof as defined herein for the manufacture of a medicament useful for inhibiting HCV activity in a mammal infected with flaviviruses, in particular HCV. In another embodiment, the present invention relates to the use of formula (V) or any subgroup thereof as defined herein for the manufacture of a medicament useful for inhibiting HCV activity in a mammal infected with flaviviruses, wherein said HCV is inhibited in its replication.

Also, the combination of previously known anti-HCV compound, such as, for instance, interferon-α (IFN-α), pegylated interferon-α and/or ribavirin, and a compound of the present invention can be used as a medicine in a combination therapy. The term "combination therapy" relates to a product containing mandatory (a) a compound of the present invention, and (b) optionally another anti-HCV compound, as a combined preparation for simultaneous, separate or sequential use in treatment of HCV infections, in particular, in the treatment of infections with HCV type 1. Thus, to combat or treat HCV infections, the compounds of this invention may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (V) or any subgroup thereof as defined above for the manufacture of a medicament useful for inhibiting HCV activity in a mammal infected with HCV viruses, wherein said medicament is used in a combination therapy, said combination therapy preferably comprising a compound of formula (V) and (pegylated) IFN-α and/or ribavirin.

It will be appreciated by the person skilled in the art that the compounds of formula (V) may be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

All patents, patent applications and articles referred to before or below are incorporated herein by reference.

EXAMPLES

The following examples are intended to illustrate, but not to limit the invention.

Example 1

Synthesis of 2-(5-bromo-2-fluorophenyl)-4-(4-pyridylamino)pteridine, Compound No. 1

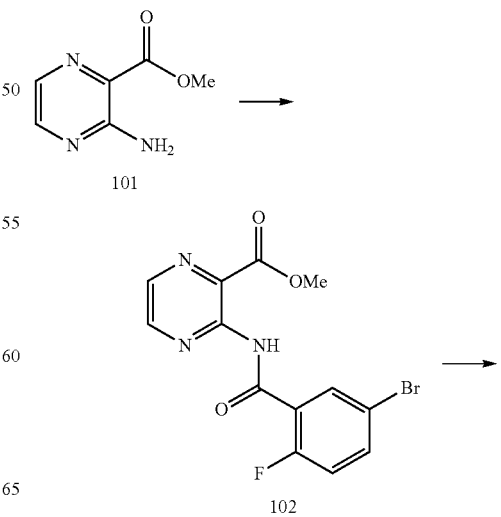

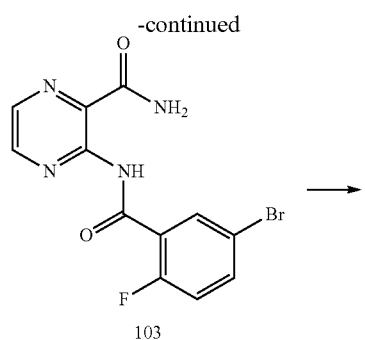

103

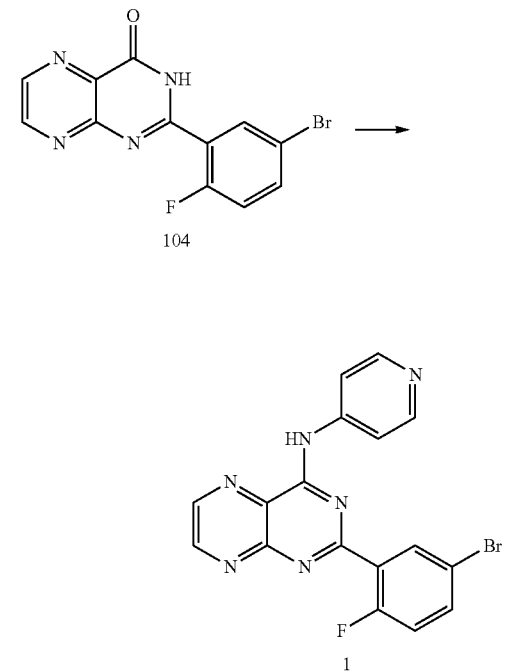

and NH₄OH (15 mL) in ethanol (50 mL) was heated at reflux for 10 min. Then, the reaction mixture was cooled at room temperature and the precipitate was filtered off, washed with ethanol and ether to give 2.1 g of the title product 103 as a white powder (LCMS analysis).

2-(5-bromo-2-fluorophenyl)pteridin-4-one 104

A mixture of 3-(5-bromo-2-fluorobenzoylamino)pyrazine-2-carboxamide 103 (2.3 g, 6.78 mmol) and KOH (3.81 g, 67.8 mmol) in H₂O (60 mL) and DMSO (20 mL) was stirred at room temperature for 45 min. Acidification to pH 5 (pH paper control) with AcOH followed by addition of 50 mL of ice-cold water afforded a precipitate, which was filtered off, washed with H₂O, acetonitrile and ether to give 1.83 g of the title product 104 as a white powder (LCMS analysis).

2-(5-bromo-2-fluorophenyl)-4-(4-pyridylamino)pteridine, Compound No. 1

Triethylamine (1.04 mL, 7.17 mmol) was added to a solution of 2-(5-bromo-2-fluoro-phenyl)pteridin-4-one 104 (800 mg, 2.49 mmol), 4-aminopyridine (469 mg, 4.98 mmol) and PyBOP (2.59 g, 4.98 mmol) in CH₂Cl₂. After 12 h, the reaction mixture was partitioned between CH₂Cl₂/Petroleum ether (2:1, 300 mL) and ice-cold 1N HCl (300 mL). The pH of the water phase was adjust to 12 with conc. NaOH and extracted with AcOEt, dried (Na₂SO₄) and evaporated. The residue was triturated in CH₂Cl₂/Petroleum ether (2:1, 15 mL), filtered off, and washed with ether. The product was purified by column chromatography (AcOEt/CH₂Cl₂/MeOH, 5:4:1) to give 325 mg of the title product 1 as a yellow powder (LCMS analysis).

Example 2

Synthesis of 4-[[2-(5-Bromo-2-fluorophenyl)pteridin-4-yl]amino]nicotinic acid, Compound No. 16, and 4-[[2-(5-bromo-2-fluorophenyl)pteridin-4-yl]amino]-N-[3-(2-oxopyrrolidin-1-yl)propyl]nicotinamide, Compound No. 21

3-(5-bromo-2-fluorobenzoylamino)pyrazine-2-carboxylic acid methyl ester 102

Pyridine (7.75 g, 98.0 mmol) was added at 0° C. under N₂ to a solution of 3-amino-pyrazine-2-carboxylic acid methyl ester 101 (1.5 g, 9.80 mmol) and 5-bromo-2-fluorobenzoylchloride (9.45 g, 49.0 mmol) in CH₂Cl₂. The reaction mixture was warmed at 40° C. for 4 h, then cooled down at room temperature. The reaction mixture was quenched with 20 mL of ethanol, evaporated, partitioned between CH₂Cl₂ and 1N NaHCO₃, dried (Na₂SO₄) and evaporated. The crude material was triturated in EtOH, filtered, washed with EtOH and ether to give 2.6 g of 3-(5-bromo-2-fluorobenzoyl-amino)pyrazine-2-carboxylic acid methyl ester 102 as a white powder (LCMS analysis).

3-(5-bromo-2-fluorobenzoylamino)pyrazine-2-carboxamide 103

A mixture of 3-(5-bromo-2-fluorobenzoylamino)pyrazine-2-carboxylic acid methyl ester 102 (2.6 g, 7.34 mmol)

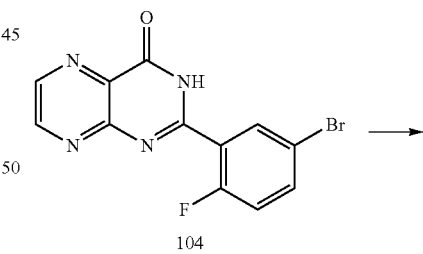

104

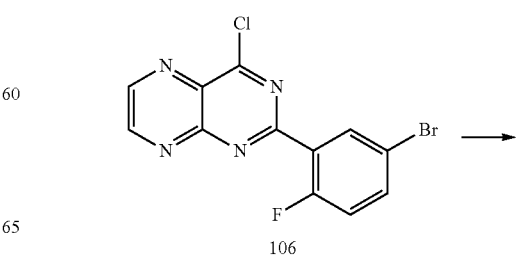

106

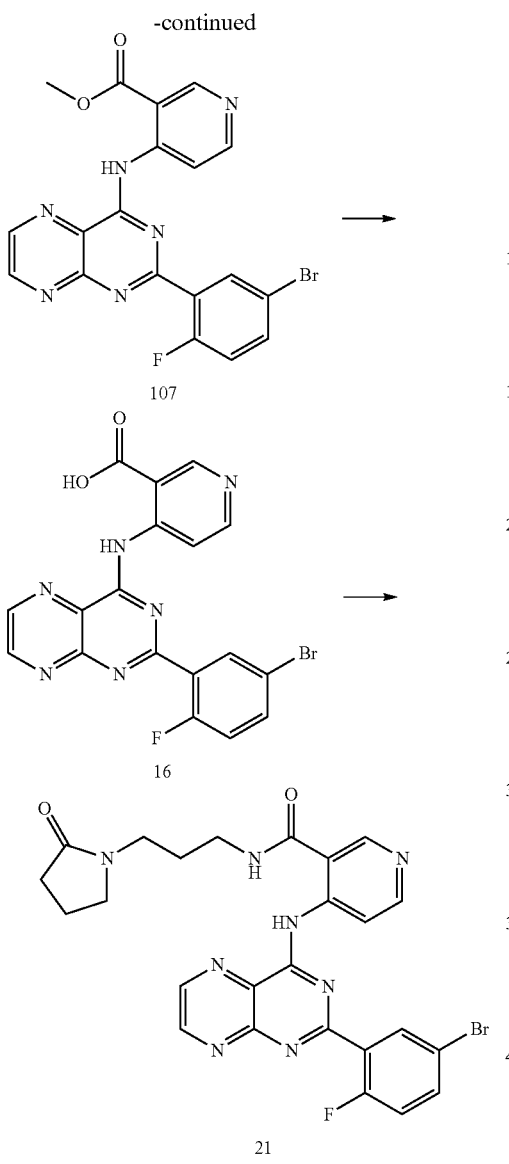

from AcOEt/Et$_2$O afforded 200 mg of the title product 107 as yellow prisms (LCMS analysis).

4-[[2-(5-Bromo-2-fluorophenyl)pteridin-4-yl]amino] nicotinic acid 16

A solution of 4-[[2-(5-bromo-2-fluorophenyl)pteridin-4-yl]amino]nicotinic acid methyl ester 107 (200 mg, 0.439 mmol) and NaOH (44 mg, 1.10 mmol) in THF/MeOH/H$_2$O (3:2:1, 5 mL), was stirred at room temperature for 3 h. The solvent was evaporated, and the residue dissolved in H$_2$O, neutralized with AcOH, filtered off, and successively washed with H$_2$O, MeOH and Ether to give 160 mg of the title product 16 as a yellow powder (LCMS analysis).

4-[[2-(5-bromo-2-fluorophenyl)pteridin-4-yl]amino]-N-[3-(2-Oxopyrrolidin-1-yl)-propyl]nicotinamide 21

Triethylamine (140 µL, 1.00 mmol) was slowly added to a solution of 4-[[2-(5-bromo-2-fluorophenyl)pteridin-4-yl]amino]nicotinic acid 16 (150 mg, 0.340 mmol), PyBOP (0.350 mg, 0.68 mmol), and 1-(β-aminopropyl)pyrrolidinone (97 mg, 0.68 mmol) in CH$_2$Cl$_2$ (10 mL). After 15 min at room temperature, the reaction mixture was evaporated and the residue purified by column chromatography (AcOEt/CH$_2$Cl$_2$, 2:1+1% triethylamine to AcOEt/CH$_2$Cl$_2$/MeOH, 7:2:1+1% triethylamine). The yellow powder was recrystallized from EtOH to give 58 mg of the title product 21 as yellow prisms (LCMS analysis).

Example 3

Synthesis of 2-(5-Bromo-2-pyrrolidin-1-ylphenyl)-4-(3-methyl-4-pyridylamino)pteridine, Compound No. 6

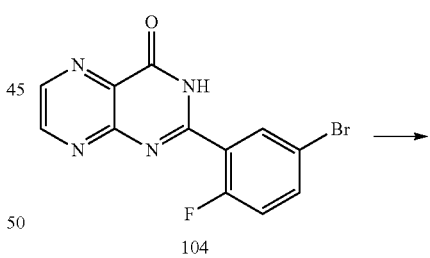

2-(5-Bromo-2-fluorophenyl)-4-Chloropteridine 106

Thionyl chloride (371 mg, 3.11 mmol) was added to the stirred suspension of 2-(5-bromo-2-fluorophenyl)pteridin-4-one 104 (200 mg, 0.623 mmol) in chloroform (5 mL) and dry DMF (100 µL). The reaction mixture was refluxed under nitrogen for 1 h (starting material gone by HPLC). The solvent was removed in vacuo. Then the residue was triturated in Et$_2$O and filtered off to give 210 mg of the title product 106 as a yellow solid (LCMS analysis).

4-[[2-(5-Bromo-2-fluorophenyl)pteridin-4-yl]amino] nicotinic acid methyl ester 107

To a solution of 2-(5-bromo-2-fluorophenyl)-4-chloropteridine 106 (200 mg, 0.589 mmol), 4-aminonicotinic acid methyl ester (224 mg, 1.47 mmol) in dichloroethane (5 mL), was added dropwise triethylamine (300 µL, 2.07 mmol). The resulting mixture was heated at 70° C. for 15 min, then quenched with silica and purified by column chromatography (AcOEt/CH$_2$Cl$_2$/triethylamine, 70/19/1). Crystallization

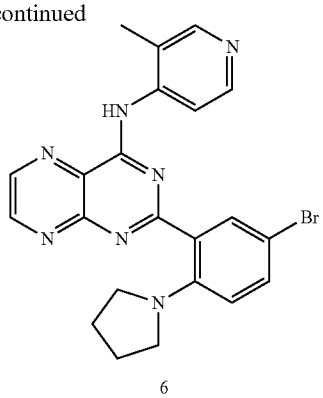

2-(5-Bromo-2-pyrrolidin-1-ylphenyl)pteridin-4-one 110

A solution of 2-(5-bromo-2-fluorophenyl)pteridin-4-one 104 in pyrrolidine was heated in a microwave cavity (Power=270 W, Temp=110° C.) for 12 min. The pyrrolidine was evaporated, then residue partitioned between NaHCO$_3$ 0.5 N and CH$_2$Cl$_2$, dried (Na$_2$SO$_4$) and evaporated. Trituration in Et$_2$O afforded the title product 110 as a yellow powder (LCMS analysis).

2-(5-Bromo-2-pyrrolidin-1-ylphenyl)-4-(3-methyl-4-pyridylamino)pteridine 6

The title product was synthesized by reaction of the 2-(5-bromo-2-pyrrolidin-1-yl-phenyl)pteridin-4-one 110 and 4-amino-3-methylpyridine following the procedure described for 4-(4-pyridylamino)-2-(5-bromo-2-fluorophenyl)pteridine 1 (LCMS analysis).

Example 4

Synthesis of 4-[(butyl)(4-pyridyl)amino]-2-(5-bromo-2-fluorophenyl)pteridine, Compound No. 3

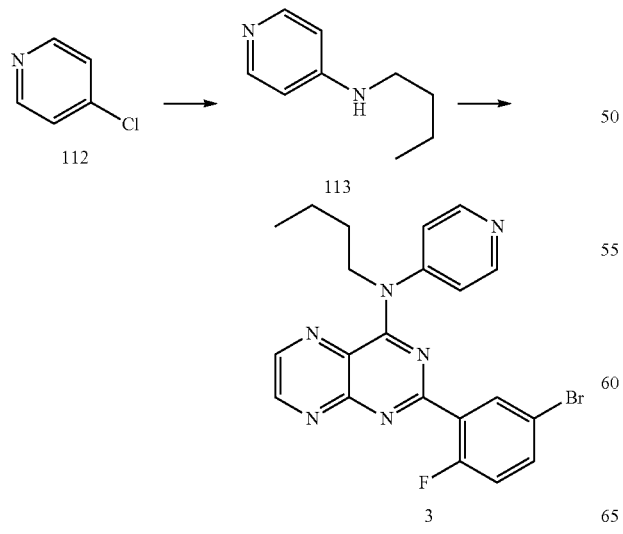

4-butylaminopyridine 113

A solution of 4-chloropyridine (2.0 g, 17.6 mmol), 50% butylamine in water (30 mL) was heated at 150° C. in a sealed tube for 24 h. The reaction mixture was evaporated, partitioned between 0.1 N NaOH and CH$_2$Cl$_2$, dried (Na$_2$SO$_4$) and evaporated. Crystallization in ether/petroleum ether 4:1 afforded 2.4 g of the title product 113 as a white powder (LCMS analysis).

4-[(butyl)(4-pyridyl)amino]-2-(5-bromo-2-fluorophenyl)pteridine 3

The title product was synthesized by reaction of the 2-(5-bromo-2-fluorophenyl)-pteridin-4-one 104 with 4-butylaminopyridine 113 following the procedure described for 4-(4-pyridylamino)-2-(5-bromo-2-fluorophenyl)pteridine 1 (LCMS analysis).

Example 5

Synthesis of 2-(3-fluorophenyl)-4-(4-pyridylamino)pteridine, Compound No. 27

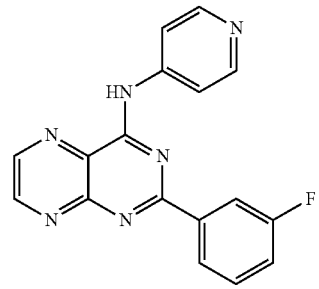

The title product was synthesized by reaction of the 2-(3-fluorophenyl)pteridin-4-one with 4-aminopyridine following the procedure described for 4-[(butyl)(4-pyridyl)-amino]-2-(5-bromo-2-fluorophenyl)pteridine 3.

Example 6

Synthesis of 2-(5-bromo-2-fluorophenyl)-4-[(methyl)(4-pyridyl)amino]pteridine, Compound No. 2

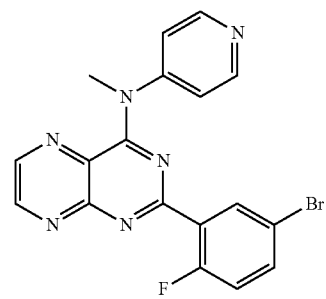

The title product was synthesized by reaction of the 2-(5-bromo-2-fluorophenyl)-pteridin-4-one 104 with 4-(methylamino)pyridine following the procedure described for 4-[(butyl)(4-pyridyl)amino]-2-(5-bromo-2-fluorophenyl)pteridine 3.

Example 7

Synthesis of 2-(5-bromo-2-fluorophenyl)-4-[(3,3-dimethylbutyl)(4-pyridyl)amino]pteridine, Compound No. 4

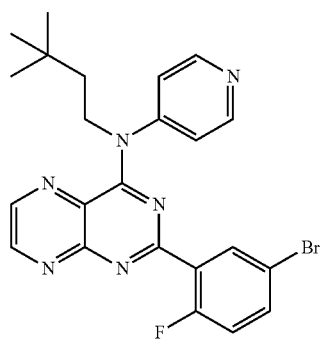

4

The title product was synthesized by reaction of the 2-(5-bromo-2-fluorophenyl)-pteridin-4-one 104 with 4-(3,3-dimethylbutylamino)pyridine following the procedure described for 4-[(butyl)(4-pyridyl)amino]-2-(5-bromo-2-fluorophenyl)pteridine 3.

Example 8

Synthesis of 4-[(benzyl)(4-pyridyl)amino]-2-(5-bromo-2-fluorophenyl)pteridine, Compound No. 5

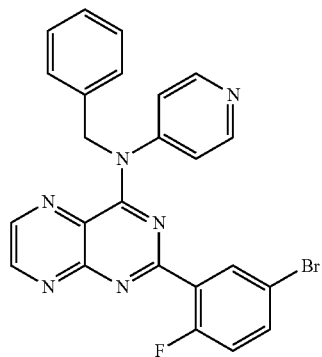

5

The title product was synthesized by reaction of the 2-(5-bromo-2-fluorophenyl)-pteridin-4-one 104 with 4-(benzylamino)pyridine following the procedure described for 4-[(butyl)(4-pyridyl)amino]-2-(5-bromo-2-fluorophenyl)pteridine 3.

Example 9

Synthesis of 2-(5-bromo-2-fluorophenyl)-4-(3-methyl-4-pyridylamino)pteridine, Compound No. 7

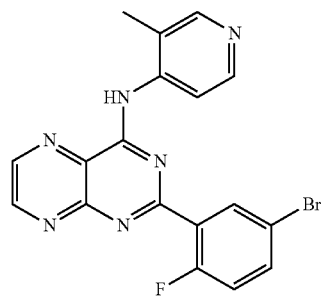

7

The title product was synthesized by reaction of the 2-(5-bromo-2-fluorophenyl)-pteridin-4-one 104 with 4-amino-3-methylpyridine following the procedure described for 4-[(butyl)(4-pyridyl)amino]-2-(5-bromo-2-fluorophenyl)pteridine 3.

Example 10

Synthesis of 2-(5-bromo-2-fluorophenyl)-4-(phenylamino)pteridine, Compound No. 8

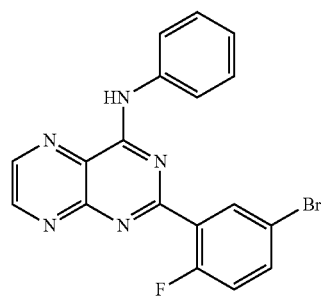

8

The title product was synthesized by reaction of the 2-(5-bromo-2-fluorophenyl)-pteridin-4-one 104 with aniline following the procedure described for 4-[(butyl)-(4-pyridyl)amino]-2-(5-bromo-2-fluorophenyl)pteridine 3.

Example 11

Synthesis of 2-(5-bromo-2-fluorophenyl)-4-(2-tolylamino)pteridine, Compound No. 9

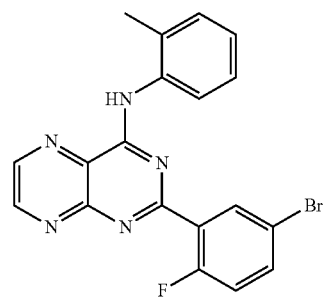

The title product was synthesized by reaction of the 2-(5-bromo-2-fluorophenyl)-pteridin-4-one 104 with 2-methylaniline following the procedure described for 4-[(butyl)(4-pyridyl)amino]-2-(5-bromo-2-fluorophenyl)pteridine 3.

Example 12

Synthesis of 2-(5-bromo-2-fluorophenyl)-4-[4-(2-pyridyl)piperazin-1-yl]pteridine, Compound No. 12

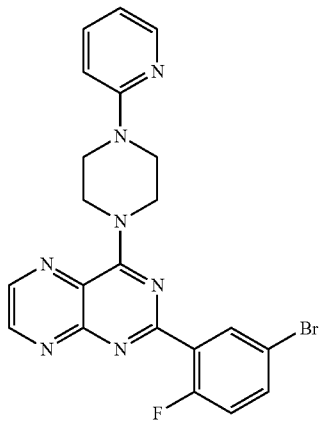

The title product was synthesized by reaction of the 2-(5-bromo-2-fluorophenyl)-pteridin-4-one 104 with 1-(2-pyridyl)piperazine following the procedure described for 4-[(butyl)(4-pyridyl)amino]-2-(5-bromo-2-fluorophenyl)pteridine 3.

Example 13

Synthesis of 2-(5-bromo-2-fluorophenyl)-4-[(methyl)(phenyl)amino]pteridine, Compound No. 10

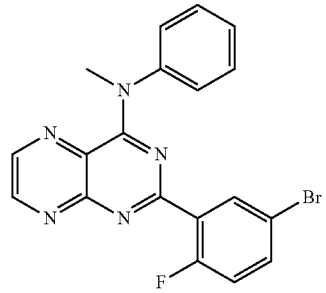

The title product was synthesized by reaction of the 2-(5-bromo-2-fluorophenyl)-pteridin-4-one 104 with N-methylaniline following the procedure described for 4-[(butyl)(4-pyridyl)amino]-2-(5-bromo-2-fluorophenyl)pteridine 3.

Example 14

Synthesis of 2-(5-bromo-2-fluorophenyl)-4-(2-hydroxyethylamino)pteridine, Compound No. 11

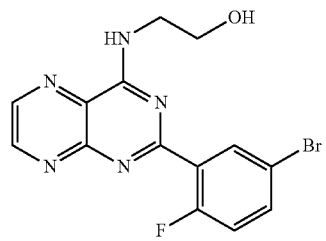

The title product was synthesized by reaction of the 2-(5-bromo-2-fluorophenyl)-pteridin-4-one 104 with 2-hydroxyethylamine following the procedure described for 4-[(butyl)(4-pyridyl)amino]-2-(5-bromo-2-fluorophenyl)pteridine 3.

Example 15

Synthesis of 2-(5-bromo-2-fluorophenyl)-4-(4-morpholinophenylamino)pteridine, Compound No. 14

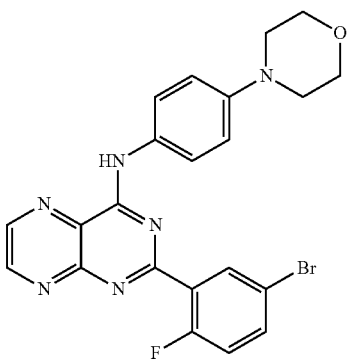

The title product was synthesized by reaction of the 2-(5-bromo-2-fluorophenyl)-pteridin-4-one 104 with 4-(4-mor-

Example 16

Synthesis of 2-(5-bromo-2-fluorophenyl)-4-(2-methyl-4-pyridylamino)pteridine, Compound No. 15

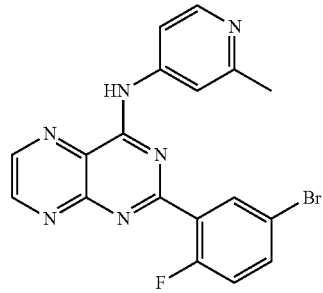

15

The title product was synthesized by reaction of the 2-(5-bromo-2-fluorophenyl)-pteridin-4-one 104 with 4-amino-2-methylpyridine following the procedure described for 4-[(butyl)(4-pyridyl)amino]-2-(5-bromo-2-fluorophenyl)pteridine 3.

Example 17

Synthesis of 2-(5-bromo-2-fluorophenyl)-4-[[2-(pyrrolidin-1-yl)ethyl]-(4-pyridyl)-amino]pteridine, Compound No. 17

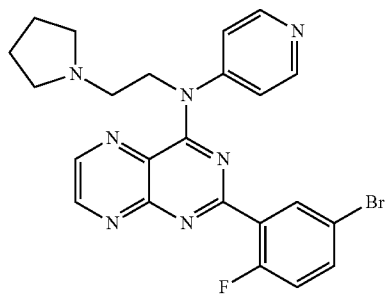

17

The title product was synthesized by reaction of the 2-(5-bromo-2-fluorophenyl)-pteridin-4-one 104 with 4-[2-(pyrrolidin-1-yl)ethylamino]pyridine following the procedure described for 4-[(butyl)(4-pyridyl)amino]-2-(5-bromo-2-fluorophenyl)-pteridine 3.

Example 18

Synthesis of 2-(5-bromo-2-fluorophenyl)-4-[(phenethyl)(4-pyridyl)amino]-pteridine, Compound No. 22

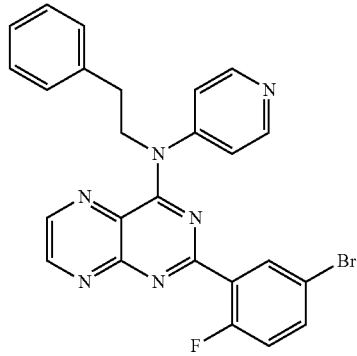

22

The title product was synthesized by reaction of the 2-(5-bromo-2-fluorophenyl)-pteridin-4-one 104 with 4-(phenethylamino)pyridine following the procedure described for 4-[(butyl)(4-pyridyl)amino]-2-(5-bromo-2-fluorophenyl)pteridine 3.

Example 19

Synthesis of 2-(2-methyl-6-pyridyl)-4-[(3-methyl-4-pyridyl)amino]pteridine, Compound No. 19

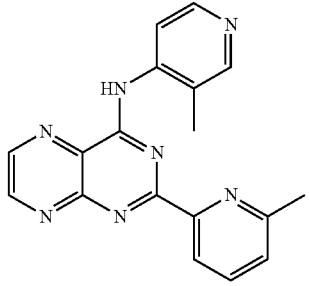

19

The title product was synthesized by reaction of the 2-(2-methyl-6-pyridyl)pteridin-4-one with 4-amino-3-methylpyridine following the procedure described for 4-[(butyl)-(4-pyridyl)amino]-2-(5-bromo-2-fluorophenyl)pteridine 3.

Example 20

Synthesis of 2-(3-chlorophenyl)-4-(4-pyridylamino)pteridine, Compound No. 18

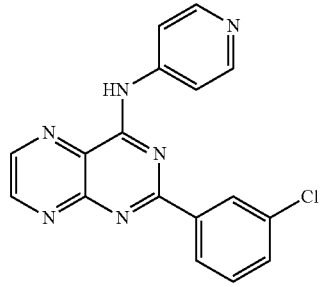

18

The title product was synthesized by reaction of the 2-(3-chlorophenyl)pteridin-4-one with 4-aminopyridine following the procedure described for 4-[(butyl)(4-pyridyl)amino]-2-(5-bromo-2-fluorophenyl)pteridine 3.

Example 21

Synthesis of 2-(5-chloro-2-fluorophenyl)-4-(3-ethyl-4-pyridylamino)pteridine, Compound No. 23

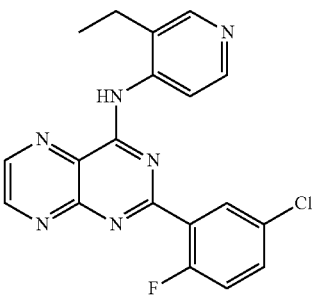

The title product was synthesized by reaction of the 2-(5-chloro-2-fluorophenyl)-pteridin-4-one with 4-amino-3-ethylpyridine following the procedure described for 4-[(butyl)(4-pyridyl)amino]-2-(5-bromo-2-fluorophenyl)pteridine 3.

Example 22

Synthesis of 2-(5-chloro-2-fluorophenyl)-4-(3-methyl-4-pyridylamino)pteridine, Compound No. 25

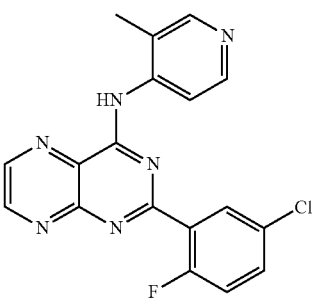

The title product was synthesized by reaction of the 2-(5-chloro-2-fluorophenyl)-pteridin-4-one with 4-amino-3-methylpyridine following the procedure described for 4-[(butyl)(4-pyridyl)amino]-2-(5-bromo-2-fluorophenyl)pteridine 3.

Example 23

Synthesis of 2-(5-chloro-2-fluorophenyl)-4-(4-pyridylamino)pteridine, Compound No. 24

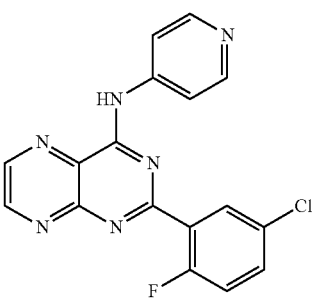

The title product was synthesized by reaction of the 2-(5-chloro-2-fluorophenyl)-pteridin-4-one with 4-aminopyridine following the procedure described for 4-[(butyl)(4-pyridyl)amino]-2-(5-bromo-2-fluorophenyl)pteridine 3.

Example 24

Synthesis of 2-(3-trifluoromethylphenyl)-4-(4-pyridylamino)pteridine, Compound No. 26

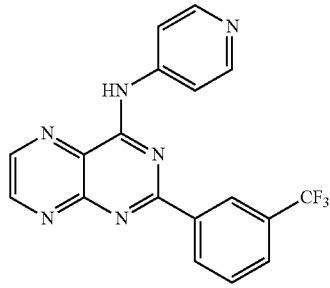

The title product was synthesized by reaction of the 2-(3-trifluoromethylphenyl)-pteridin-4-one with 4-aminopyridine following the procedure described for 4-[(butyl)(4-pyridyl)amino]-2-(5-bromo-2-fluorophenyl)pteridine 3.

In Table 2 below, the LCMS data for the synthetized compounds is shown:

| Compound Number | LCMS data |
| --- | --- |
| 1 | m/z: 397, 398, 399, 400 RT: 2.30 |
| 13 | m/z: 455, 456, 457, 458, RT: 4.06 |
| 21 | m/z: 565, 566, 567, 568, RT: 3.12 |
| 6 | m/z: 462, 463, 464, 465, RT: 2.73 |
| 3 | m/z: 453, 454, 455, 456, RT: 3.45 |
| 2 | m/z: 411, 412, 413, 414, RT = 2.49 |
| 4 | m/z: 481, 482, 483, 484, RT = 4.23 |
| 5 | m/z: 487, 488, 489, 490, RT: 3.49 |
| 7 | m/z: 411, 412, 413, 414, RT: 2.49 |
| 8 | m/z: 396, 397, 398, 399, RT: 4.52 |
| 9 | m/z: 410, 411, 412, 413, RT: 4.59 |
| 12 | m/z: 466, 467, 468, 469, RT: 3.31 |
| 10 | m/z: 410, 411, 412, 413, RT: 4.70 |
| 11 | m/z: 364, 365, 366, 367, RT = 2.67 |
| 14 | m/z: 419, 420, RT: 4.27 |
| 15 | m/z: 411, 412, 413, 414, RT: 2.49 |
| 22 | m/z: 501, 502, RT: 3.50 |
| 19 | m/z: 330, RT: 1.40 |
| 18 | m/z: 335, 336, 337, RT: 2.37 |
| 25 | m/z: 367, 368, 369, RT: 2.44 |
| 24 | m/z: 353, 354, 355, RT: 2.29 | m/z is the mass-to-charge ratio
RT is the retention time

Example 25

Activity of Compounds of Formula (V) in HCV Replicon Assays

Stable Replicon Cell Reporter Assays:

The compounds of the present invention are examined for activity in the inhibition of HCV RNA replication in a cellular assay. The assay demonstrates that the present compounds exhibit activity against HCV replicons functional in a cell culture. The cellular assay is based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method is as follows.

The assay utilizes the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

Cellular Assay Experimental Method:

The replicon cells are plated in 384 well plates in the presence of the test and control compounds which are added in various concentrations. Following an incubation of three days, HCV replication is measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity is monitored on the Huh-Luc cells, enabling a dose-response curve for each test compound. EC50 values are then calculated, which value represents the amount of the compound required to decrease by 50% the level of detected luciferase activity, or more specifically, the ability of the genetically linked HCV replicon RNA to replicate.

The compounds tested were found to have activities as follows:

TABLE 3

| Compound Number | HCV Replicon activity (µM) |
|---|---|
| 1 | 0.352 |
| 13 | 4.9 |
| 21 | 0.058 |
| 6 | 18 |
| 3 | 2.2 |
| 27 | 3.0 |
| 2 | 3.65 |
| 4 | 0.48 |
| 5 | 0.99 |
| 7 | 0.95 |
| 8 | >32 |
| 9 | 11 |
| 12 | >32 |
| 10 | 11 |
| 11 | >32 |
| 14 | 8.7 |
| 15 | 3.56 |
| 22 | 1.96 |
| 19 | 12 |
| 18 | 1.5 |
| 23 | 0.52 |
| 25 | 0.48 |
| 24 | 0.78 |
| 26 | 2.0 |

Example 26

Pharmacokinetic Profile of Compound Nr. 21 in Male Swiss SPF (CD1)-mice

Compound nr. 21 was dissolved in a 10% hydroxypropyl-β-cyclodextrin (HP-β-CD) solution at a final concentration of 1 mg base-eq./ml, .pH 4.36.

Three animals were administered orally the solution of compound nr. 21 to obtain a dose of 20 mg base-eq./kg. Blood samples were taken at 30 min, 1, 2, 4, 8 and 24 h after oral dose administration. Plasma was obtained following centrifugation at 4° C. for 10 minutes at approximately 1900×g.

From each orally dosed animal individual samples of heart and liver were dissected and weighed. Tissue samples were homogenized in demineralized water.

Plasma and tissue samples were analysed for compound nr. 21, using a qualified research LC-MS/MS method.

A limited pharmacokinetic analysis was performed using WinNonlin™ Professional (Version 4.0.1). A non-compartmental analysis using the lin/log trapezoidal rule with lin/log interpolation was used for all data. The variability between animals is indicated by the standard deviation (st dev).

An overview of the mean plasma and tissue concentrations and some basic pharmacokinetic parameters can be found in Table 4 and FIG. 1.

Conclusion: The analysed concentration of the oral formulation was 1.0 mg base-eq./ml resulting in an exact dose of 20 mg base-eq./kg orally. No stability problems were observed on the day of dosing.

Plasma

After a single oral administration of the compound nr 21 at 20 mg base-eq./kg levels were quantifiable up to 8 h post dose (Table 4 and FIG. 1). The mean maximum plasma concentration ($C_{max}$) was 220 ng/ml observed at 0.5 h post dose ($T_{max}$), indicating a rapid absorption of the compound. The mean half-life ($t_{1/2(2-8h)}$) was 2.9 h.

The exposure as calculated by $AUC_{0-inf}$ was 332 ng.h/ml.

Tissue

As can be seen in FIG. 1, the studied tissues together with plasma had quite similar concentration time profiles, indicating distribution equilibrium between plasma and tested tissues. The mean maximum tissue concentrations ($C_{max}$) were achieved at the same time as in plasma at 0.5 h post dose, indicating a rapid equilibrium. The highest concentration was observed in the liver (4057 ng/g) followed by heart (678 ng/g) with a tissue to plasma ratios of 24 and 3.8 respectively (Table 4 and FIG. 1). The mean half-life ($t_{1/2(2-8h)}$) estimated for the liver was 3.5 h and 3.4 h for the heart which was comparable with that of plasma (2.9 h). Tissue levels declined in a similar pattern to plasma and at 8 h post dose only low levels of the compound were still detectable, indicating no major evidence for retention.

TABLE 4

Mean plasma and tissue levels (n = 3) together with some basic pharmacokinetic parameters of compound nr. 21 after a single oral administration at 20 mg base-eq./kg in the male Swiss SPF (CD1)-mice Compound nr. 21 (ng/ml or g/ml)

| Time | Plasma | stdev | Heart | stdev | Liver | stdev |
|---|---|---|---|---|---|---|
| 0.5 | 220 | ±100 | 678 | ±258 | 4057 | ±1730 |
| 1 | 166 | ±160 | 557 | ±403 | 2937 | ±1852 |
| 2 | 21.7 | ±6.7 | 92.9 | ±49.9 | 611 | ±131 |
| 4 | 20.3 | ±5.1 | 83.6 | ±35.9 | 627 | ±189 |

TABLE 4-continued

Mean plasma and tissue levels (n = 3) together with some basic pharmacokinetic parameters of compound nr. 21 after a single oral administration at 20 mg base-eq./kg in the male Swiss SPF (CD1)-mice

| | Compound nr. 21 (ng/ml or g/ml) | | | | | |
|---|---|---|---|---|---|---|
| Time | Plasma | stdev | Heart | stdev | Liver | stdev |
| 8 | 5.52 | ±1.20 | 29.1 | ±6.0 | 201 | ±59 |
| 24 | BQL[1] | | BQL[1] | | BQL[1] | |
| $C_{max}$ (ng/ml) | 220 | | 678 | | 4057 | |
| $T_{max}$ (h) | 0.5 | | 0.5 | | 0.5 | |
| $t_{1/2(2-8\,h)}$ (h) | 2.9 | | 3.4 | | 3.5 | |
| $AUC_{(0-8\,h)}$ (ng · h/ml) | 309 | | 1119 | | 6965 | |
| $AUC_{0-inf}$ (ng · h/ml) | 332 | | 1262 | | 7973 | |
| Ratio tissue/ plasma | — | | 3.8[2] | | 24[2] | |

[1]BQL = below the limit of quantification. LLOQ was 0.500 ng/ml for plasma and ranged between 5.00 and 13.16 ng/g for tissue.
[2]value based upon the $AUC_{inf}$

The invention claimed is:
1. A method of treating hepatitis C virus (HCV) infection comprising
administering to a mammal identified as infected with HCV, wherein the mammal does not have liver fibrosis, chronic hepatitis, and/or cirrhosis, a compound having the formula (I) for a time and in an amount effective to diminish HCV viral load in the mammal

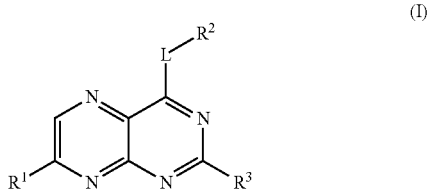

(I)

or an N-oxide, salt, stereoisomeric form, racemic mixture, prodrug, ester or metabolite thereof, wherein
$R^1$ is independently hydrogen, amino, mono- or disubstituted amino, wherein the substituent(s) of the amino may be selected from $C_{1-6}$alkyl, $C_{2-6}$alkenyl, $C_{2-6}$alkynyl, $C_{1-4}$alkoxy$C_{1-4}$alkyl, di$C_{1-4}$alkylamino$C_{1-4}$alkyl, piperidin-1-yl-$C_{1-4}$alkyl, aryl$C_{1-6}$alkyl, wherein the aryl group may be further substituted with $C_{1-4}$alkyl, or $C_{1-4}$alkoxy;
L is —$NR^8$—, —$NR^8$—$C_{1-6}$alkanediyl-, —$NR^8$—CO—$C_{1-6}$alkanediyl-, —$NR^8$—$SO_2$—$C_{1-6}$alkanediyl-, —O—, —O—$C_{1-6}$alkanediyl-, —O—CO—, —O—CO-$C_{1-6}$alkanediyl-, —S—, —S—$C_{1-6}$alkanediyl-, or

wherein the dotted ring together with N and Z form a $Het^1$ cycle having 5 to 8 members including ring members N and Z, and wherein said L ring is attached to the pteridine ring by the nitrogen atom;
Z is N or CH;
$R^2$ is hydrogen, hydroxy$C_{1-6}$alkyl, $C_{3-7}$cycloalkyl, aryl, $Het^1$, or $Het^2$, wherein said $C_{3-7}$cycloalkyl, aryl, $Het^1$, and $Het^2$ are each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, and aminophenylcarbonyl, and wherein the $C_{1-4}$alkyl may be further substituted with —$COOR^7$;
$R^3$ is a $C_{1-6}$alkyl, $C_{3-7}$cycloalkyl, aryl, aryl$C_{1-6}$alkyl, $Het^1$, $Het^2$ or $Het^2$-$C_{1-6}$alkyl, each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}COOR^7$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$; and wherein $R^{4a}$ and $R^{4b}$ may optionally form, together with the nitrogen atom to which they are bound, a 5 to 8 membered saturated, unsaturated or partially unsaturated ring, optionally comprising one or two additional heteroatoms;
each $R^{4a}$ and $R^{4b}$ is independently hydrogen, $C_{1-4}$alkyl, hydroxy$C_{1-4}$alkyl, $Het^1$-$C_{1-4}$alkyl, polyhalo$C_{1-4}$alkyl, cyano, or nitro;
each $R^5$ is independently hydrogen, or $C_{1-4}$alkyl;
each $R^6$ is independently hydrogen, or $C_{1-4}$alkyl;
each $R^7$ is independently hydrogen, or $C_{1-4}$alkyl; and
$R^8$ is hydrogen, $C_{1-10}$alkyl, $C_{2-10}$alkenyl, $C_{2-10}$alkynyl, $C_{1-10}$alkylcarbonyl, amino-$C_{1-10}$alkyl, aryl, arylcarbonyl, aryl$C_{1-10}$alkyl, $Het^1$, $Het^1C_{1-6}$alkyl, or a protecting group, wherein the aryl is optionally substituted with 1 to 3 substituents selected from $C_{1-4}$alkyl, $C_{2-4}$alkenyl, $C_{2-4}$alkynyl, $C_{1-4}$alkylcarbonyl, phenyl, $C_{1-4}$alkylphenyl, phenylcarbonyl, aminophenyl, amino-$C_{1-4}$alkylphenyl, aminophenylcarbonyl, halo, —$OR^6$, —$NR^{4a}R^{4b}$, —$SR^5$, —$SOR^5$, —$NR^{4a}SOR^5$, —$NR^{4a}SO_2R^5$, —$SO_2R^5$, —$OCOR^6$, —$NR^{4a}COR^6$, —$NR^{4a}CONR^{4a}R^{4b}$, —$NR^{4a}COOR^6$, —$OCONR^{4a}R^{4b}$, —$COOR^6$, —$SO_3R^6$, —$CONR^{4a}R^{4b}$, —$SO_2NR^{4a}R^{4b}$, cyano, polyhalo-$C_{1-4}$alkyl, and nitro;
$Het^1$ as a group or part of a group is defined as a saturated or partially unsaturated monocyclic, bicyclic or tricyclic heterocycle having 3 to 12 ring members, which contains one or more heteroatom ring members selected from nitrogen, oxygen or sulfur and which is optionally substituted on one or more carbon atoms by $C_{1-6}$alkyl, $C_{1-6}$alkoxy, halo, hydroxy, oxo, optionally mono- or disubstituted amino, nitro, cyano, polyhalo$C_{1-4}$alkyl, carboxyl, $C_{1-6}$alkoxy-carbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are hydrogen, or $C_{1-4}$alkyl;
$Het^2$ as a group or part of a group is defined as an aromatic monocyclic, bicyclic or tricyclic heterocycle having 3 to 14 ring members, which contains one or more heteroatom ring members each independently selected from nitrogen, oxygen or sulfur, and which is optionally substituted on one or more carbon atoms by $C_{1-6}$alkyl, optionally mono- or disubstituted amino$C_{1-6}$alkyl, hydroxyC$_{1-6}$alkyl, C$_{1-6}$alkoxy, halo, hydroxy, optionally mono- or disubstituted amino, nitro, cyano, polyhaloC$_{1-4}$alkyl, carboxyl, C$_{1-6}$alkoxycarbonyl, C$_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are hydrogen, or C$_{1-4}$alkyl; and aryl as a group or part of a group is phenyl.

2. The method of claim 1, wherein the compound has the formula (II)

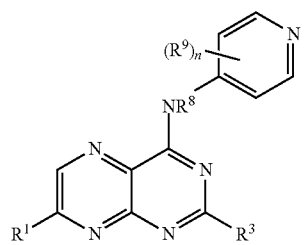

(II)

or an N-oxide, salt, stereoisomeric form, racemic mixture, prodrug, ester or metabolite thereof, and further wherein R$^9$ is C$_{1-4}$alkyl, C$_{2-4}$alkenyl, C$_{2-4}$alkynyl, polyhaloC$_{1-4}$alkyl, halo, cyano, nitro,
—COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$,
—NR$^{4a}$COR$^6$, —NR$^{4a}$CONR$^{4a}$R$^{4b}$, —NR$^{4a}$SOR$^5$, —NR$^{4a}$SO$_2$R$^5$, —SR$^5$, —SOR$^5$, —SO$_2$R$^5$,
—SO$_3$R$^7$, —SO$_2$NR$^{4a}$R$^{4b}$, morpholin-4-yl, phenyl, aminophenyl, or aminophenyl-carbonyl, and wherein the C$_{1-4}$alkyl may be further substituted with —COOR$^7$; and n is 0, 1, 2, 3, or 4.

3. The method of claim 1, wherein the compound has the formula (III):

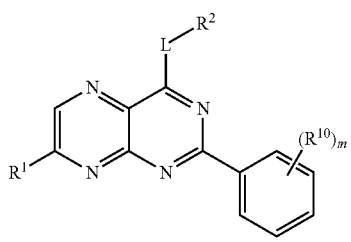

(III)

or an N-oxide, salt, stereoisomeric form, racemic mixture, prodrug, ester or metabolite thereof, and further wherein R$^{10}$ is C$_{1-4}$alkyl, C$_{2-4}$alkenyl, C$_{2-4}$alkynyl, polyhaloC$_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$,
—NR$^{4a}$COR$^6$, —NR$^{4a}$COOR$^7$, —NR$^{4a}$CONR$^{4a}$R$^{4b}$, —NR$^{4a}$SOR$^5$, —NR$^{4a}$SO$_2$R$^5$, —SR$^5$,
—SOR$^7$, —SO$_2$R$^5$, —SO$_3$R$^7$, and —SO$_2$NR$^{4a}$R$^{4b}$; and m is 0, 1, 2, 3, or 4.

4. The method of claim 1, wherein the compound has the formula (IV):

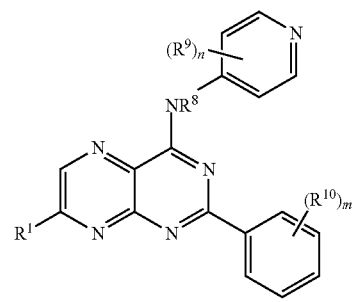

(IV)

or an N-oxide, salt, stereoisomeric form, racemic mixture, prodrug, ester or metabolite thereof, and further wherein R$^9$ is C$_{1-4}$alkyl, C$_{2-4}$alkenyl, C$_{2-4}$alkynyl, polyhaloC$_{1-4}$alkyl, halo, cyano, nitro,
—COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$,
—NR$^{4a}$COR$^6$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$,
—SO$_3$R$^7$, —SO$_2$NR$^{4a}$R$^{4b}$, morpholin-4-yl, phenyl, aminophenyl, or aminophenyl-carbonyl, and wherein the C$_{1-4}$alkyl may be further substituted with —COOR$^7$;

R$^{10}$ is C$_{1-4}$alkyl, C$_{2-4}$alkenyl, C$_{2-4}$alkynyl, polyhaloC$_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$,
—NR$^{4a}$COR$^6$, —NR$^{4a}$COOR$^7$, —NR$^{4a}$CONR$^{4a}$R$^{4b}$, —NR$^{4a}$SOR$^5$, —NR$^{4a}$SO$_2$R$^5$, —SR$^5$,
—SOR$^7$, —SO$_2$R$^5$, —SO$_3$R$^7$, and —SO$_2$NR$^{4a}$R$^{4b}$;

n is 0, 1, 2, 3, or 4; and m is 0, 1, 2, 3, or 4.

5. The method of claim 1, wherein the compound has the formula (V):

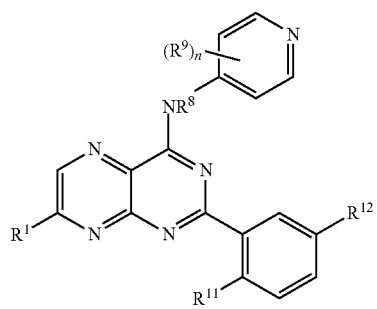

(V)

or a salt, stereoisomeric form, or racemic mixture thereof, wherein

R$^1$ is hydrogen or amino;

R$^8$ is hydrogen, C$_{1-6}$alkyl, aminoC$_{1-4}$alkyl, phenylC$_{1-4}$alkyl, pyrrolidin-1-ylC$_{1-4}$alkyl, or C$_{1-6}$alkoxycarbonyl;

each R$^9$ is, independently, hydrogen, C$_{1-4}$alkyl, —COR$^6$, —COOR$^7$, or —CONR$^{4a}$R$^{4b}$;

n is 0, 1, 2, 3, or 4;

R$^{11}$ is hydrogen, halo, or —NR$^{4a}$R$^{4b}$, wherein R$^{4a}$ and R$^{4b}$ may optionally form, together with the nitrogen atom to which they are bound, a 5 to 8 membered saturated, unsaturated or partially unsaturated ring, optionally comprising one or two additional heteroatoms;

R$^{12}$ is hydrogen, halo, C$_{1-4}$alkyl, or polyhaloC$_{1-4}$alkyl;

$R^6$ is hydrogen, or $C_{1-4}$alkyl;
$R^7$ is hydrogen, or $C_{1-4}$alkyl; and
$R^{4a}$ and $R^{4b}$, independently, are hydrogen, $C_{1-4}$alkyl, 2-oxo-pyrrolidin-1-yl-$C_{1-4}$alkyl.

6. The method of claim 5, wherein the compound has the formula (VI):

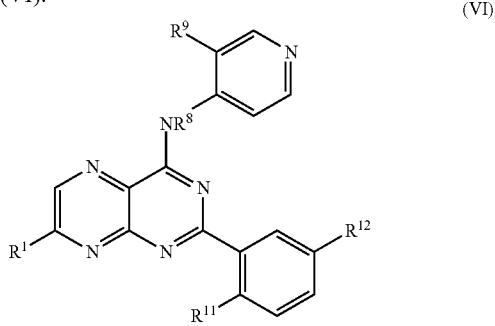

(VI)

or a salt, stereoisomeric form, or racemic mixture thereof.

7. The method of claim 1 wherein the mammal does not have liver fibrosis.

8. The method of claim 1, wherein the mammal does not have chronic hepatitis, and/or cirrhosis.

9. The method of claim 1, wherein the compounds having the formula (I) is administered in combination with another anti-HCV compound.

10. The method of claim 9, wherein the other anit-HCV compound is interferon-α, pegylated interferon-α, ribavirin, or a combination thereof.

11. The method of claim 1, wherein the HCV viral load is diminished to undetectable levels.

12. The method of claim 1, wherein the viral load is determined by detecting HCV RNA in the blood of the mammal.

* * * * *

UNITED STATES PATENT AND TRADEMARK OFFICE
CERTIFICATE OF CORRECTION

PATENT NO.         : 9,290,502 B2
APPLICATION NO.    : 14/095099
DATED              : March 22, 2016
INVENTOR(S)        : Pierre Jean-Marie Bernard Raboisson Page 1 of 1

It is certified that error appears in the above-identified patent and that said Letters Patent is hereby corrected as shown below:

Claims

COL. 47, line 34 (claim 2), delete "$SOR^5$" and substitute therefor -- $SOR^7$ --

COL. 50, line 10 (claim 10), delete "anit-HCV" and substitute therefor -- anti-HCV --

Signed and Sealed this
Twelfth Day of July, 2016

Michelle K. Lee
*Director of the United States Patent and Trademark Office*